US012778405B2

(12) United States Patent
Wales et al.

(10) Patent No.: US 12,778,405 B2
(45) **Date of Patent: *Nov. 3, 2026**

(54) DEVICES, SYSTEMS, AND METHODS TO SUPPLY FLUIDS TO AN ENDOSCOPE

(71) Applicant: Boston Scientific Scimed, Inc., Maple Grove, MN (US)

(72) Inventors: Ryan V. Wales, Northborough, MA (US); Paul Smith, Smithfield, RI (US); Jeffrey V. Bean, Fitchburg, MA (US); Samuel Olubakinde, Worcester, MA (US); Scott Edward Corbeil, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 225 days.

This patent is subject to a terminal disclaimer.

(21) Appl. No.: 18/670,904

(22) Filed: May 22, 2024

(65) Prior Publication Data

US 2024/0389843 A1 Nov. 28, 2024

Related U.S. Application Data

(60) Provisional application No. 63/504,378, filed on May 25, 2023.

(51) Int. Cl.
*A61B 1/12* (2006.01)

(52) U.S. Cl.
CPC .................................... *A61B 1/126* (2013.01)

(58) Field of Classification Search
CPC ....... A61B 1/126; A61B 1/015; A61M 3/0233
See application file for complete search history.

(56) References Cited

U.S. PATENT DOCUMENTS 5,133,336 A 7/1992 Savitt et al.
8,870,756 B2 10/2014 Maurice
11,576,566 B2 2/2023 Pollock et al.
(Continued)

FOREIGN PATENT DOCUMENTS

JP 2005245708 A 9/2005

OTHER PUBLICATIONS

International Search Report and Written Opinion for International Application No. PCT/US2024/030469, dated Sep. 19, 2024. (12 Pages).

*Primary Examiner* — John R Schnurr
(74) *Attorney, Agent, or Firm* — Seager, Tufte & Wickhem, LLP

(57) ABSTRACT

Methods and systems for providing a flow of fluid to an endoscope. An illustrative container and tube set arranged and configured to couple to an endoscope may comprise a first container configured to contain a fluid, a sealing member, a compression member, a first fluid supply tube including a first lumen in fluid communication with the sealing member and the first container, a branched connector positioned in line with first fluid supply tube and including a first fluid inlet, a first fluid outlet, and a second fluid outlet, a second container having a second fluid inlet in fluid communication with the second fluid outlet of the branched connector, a second fluid supply tube in fluid communication with the bottom portion of the second container, and a first gas supply tube in operative fluid communication with the second container.

20 Claims, 13 Drawing Sheets

(56) References Cited

U.S. PATENT DOCUMENTS

| | | | | |
|---|---|---|---|---|
| 2007/0191711 | A1* | 8/2007 | Bush | A61B 1/00082 600/437 |
| 2011/0268611 | A1* | 11/2011 | Akahori | A61B 1/125 366/173.1 |
| 2016/0135669 | A1 | 5/2016 | Boulais et al. | |
| 2021/0371175 | A1 | 12/2021 | Martella et al. | |
| 2022/0096812 | A1* | 3/2022 | Wales | A61M 39/14 |
| 2022/0192478 | A1 | 6/2022 | Pollock et al. | |
| 2022/0192479 | A1 | 6/2022 | Harris et al. | |
| 2024/0366078 | A1* | 11/2024 | Smith | A61B 1/126 |

* cited by examiner

DEVICES, SYSTEMS, AND METHODS TO SUPPLY FLUIDS TO AN ENDOSCOPE

CROSS-REFERENCE TO RELATED APPLICATIONS

This application claims the benefit of U.S. Provisional Patent Application Ser. No. 63/504,378 filed on May 25, 2023, the disclosure of which is incorporated herein by reference.

FIELD

This disclosure relates generally to medical fluid containers and methods, and particularly to a container and tube sets to supply fluid and/or gas to an endoscope.

BACKGROUND

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. For example, sterile water may be used to irrigate the working lumen during the procedure. Further, during endoscopic procedures, the video lens at the distal end of the endoscope, which is used to navigate and visualize target tissues, may be prone to becoming fouled with blood, mucous, and other debris during the procedure. In order to reduce complications that may arise from removing the endoscope, manually cleaning the lens, and re-inserting (such as trauma or infection) nearly all endoscopes may be equipped with a lumen through which a cleaning fluid (which may typically be sterile water) can be delivered to the surface of the lens for the purpose of de-fouling.

The current state of the art for devices used to deliver sterile water to the endoscope for the purpose of irrigation and endoscope lens washing draw and/or push water from either one or two disposable bottles of sterile water (typically IL volume). In the two-bottle system, two separate disposable sterile water bottles may be used to supply sterile water separately to the endoscope for irrigation or lens washing. For irrigation, a flexible conduit may extend through a cap, which can be fitted onto the sterile water bottle after opening, and to the bottom of the bottle on the inlet end, may be inserted within the drive head of a peristaltic roller pump and connected to the endoscope through a scope specific connector. In the two-bottle system, a second sterile water bottle may be fitted with a cap having an inlet tube/connector which allows pressurized air or $CO_2$ gas to enter the bottle, and having a flexible conduit which extends from the bottle to, and connecting with, the lens wash port of the endoscope via a scope specific connector. Using this system, $CO_2$ gas may be supplied to the bottle at a pre-determined pressure, which in turn creates a pressure differential, driving sterile water through the conduit to the lens wash inlet of the endoscope, such that when the lens wash switch on the endoscope is triggered, sterile water jets through a dedicated lumen within the endoscope and washes sterile water over the fouled lens, thus clearing the lens.

In the one-bottle system, a cap may be attached to a single water bottle having a first conduit extending to the bottom of the bottle and extends through the roller pump and connecting to the irrigation port of the endoscope. A second conduit may extend to the bottom of the bottle and extend to the lens wash port on the endoscope. A third conduit may bring pressurized gas (e.g., air or $CO_2$) into the bottle through a port on the cap. This system may allow a single sterile water bottle to be used for both lens wash and irrigation instead of a separate bottle for lens wash and irrigation.

Currently commercialized systems for delivering sterile water to the endoscope may rely on commercially available bottles of sterile water, with which the sterile water is pumped or pushed with compressed gas from the bottle to the scope. The volume of water available to the user is limited by the size/volume of commercially available sterile water bottles and space on procedure carts. In many hospital centers, the sterile water delivery systems may have a one-way valve at the end of the conduit to the scope to prevent backflow of fluids from the patient end of the scope back to the inlet sterile water conduit so that the sterile water delivery system may be used for multiple cases, over the course of a day.

As clinicians work through each case some volume of water is depleted from the water bottle and bottles may need to be replaced one or more times over the course of the day. The process of exchanging bottles may require the user to bend or stoop down, remove the cap and associated inlet tubes from the empty bottle, and place them into a full bottle of sterile water without touching/contaminating the tubes against the external bottle or other non-sterile surfaces (e.g., so as not to create an infection risk to the patient). This may be especially difficult in the single bottle devices where multiple inlet hoses dangle from the cap when removing the cap to replace the sterile water bottle. Further, the water bottle may leak if the cap is not threaded properly.

Additionally, the water bottle may require a level surface to be properly placed, which in an endoscopy suite is at a premium In some cases, having the sterile water bottles stowed on lower shelves of the carts, alongside the peristaltic pump, and other equipment may make these difficult to visualize and often, the clinician may not realize that the bottle is nearing empty until they are no longer able to deliver irrigation or lens wash to through the distal end of the scope. There is also an inherent risk associated with stowing the water bottles adjacent to the endoscope control boxes. For example, if the water bottle fails in some way (e.g., leak, burst, rupture, etc.) there may be a high risk of water running or spraying onto these high-cost control systems resulting in significant damage or destruction. It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example, a container and tube set arranged and configured to couple to an endoscope for use in an endoscopic procedure may comprise a first container including a neck defining an opening and a body portion, the first container configured to contain a fluid, a sealing member including a first end, a second end, and a first lumen extending therethrough, the sealing member configured to be disposed adjacent to the opening of the neck of the first container, a compression member including a first end, a second end, and a second lumen extending therethrough, the compression member configured to selectively expand the sealing member, a first fluid supply tube including a first end, a second end, and a third lumen extending therethrough, wherein the third lumen is in fluid communication with the first container, the first end is coupled to the second end of the compression member, and the second end of the first water supply tube is positioned external to the first container, a second container configured to contain a fluid, the second container having a second fluid inlet in selective fluid communication with the third lumen of the first fluid supply tube, a second fluid supply tube including a first end, a second end, and a fourth lumen extending therethrough, wherein the fourth lumen is in selective fluid communication with a bottom portion of the second container and the second end of the second water supply tube is positioned external to the second container, and a first gas supply tube including a first end, a second end, and a fifth lumen extending therethrough, wherein the fifth lumen is in operative fluid communication with the second container and the second end of the first gas supply tube is positioned external to the second container.

Alternatively or additionally to any of the examples above, in another example, the container and tube set may further comprise a third fluid supply tube including a first end, a second end, and a sixth lumen extending therethrough, wherein the sixth lumen is in selective fluid communication with the first container and a branched connector positioned in line with the first fluid supply tube, the branched connector including a first fluid inlet, a first fluid outlet, and a second fluid outlet, a portion of the third lumen of the first fluid supply tube extending between the first fluid inlet and the first fluid outlet and the sixth lumen of the third fluid supply tube in fluid communication with the second outlet.

Alternatively or additionally to any of the examples above, in another example, the sealing member may comprise an elastomeric material.

Alternatively or additionally to any of the examples above, in another example, the sealing member may be disposed within the opening of the neck of the first container.

Alternatively or additionally to any of the examples above, in another example, the sealing member may be positioned against the opening of the neck of the first container.

Alternatively or additionally to any of the examples above, in another example, the compression member may be disposed within the first lumen of the sealing member.

Alternatively or additionally to any of the examples above, in another example, the compression member may comprise a rigid material.

Alternatively or additionally to any of the examples above, in another example, the compression member may have an outer diameter that is greater than an inner diameter of the first lumen of the sealing member along at least a portion of a length of the compression member.

Alternatively or additionally to any of the examples above, in another example, the first end of the compression member may be positioned distal to the first end of the sealing member and the second end of the compression member may be positioned proximal to the second end of the sealing member.

Alternatively or additionally to any of the examples above, in another example, the compression member may comprise an actuatable member adjacent to the second end thereof.

Alternatively or additionally to any of the examples above, in another example, actuation of the actuatable member from a first position to a second position may be configured to compress and radially expand the sealing member.

Alternatively or additionally to any of the examples above, in another example, the actuatable member may be rotated.

Alternatively or additionally to any of the examples above, in another example, the actuatable member may be pivoted.

Alternatively or additionally to any of the examples above, in another example, the container and tube set may further comprise a vent tube including a first end, a second end, and a fifth lumen, the vent tube extending through the third lumen of the first fluid supply tube.

Alternatively or additionally to any of the examples above, in another example, the first end of the vent tube may be configured to extend above a fluid line of the first container.

In another example, a container and tube set arranged and configured to couple to an endoscope for use in an endoscopic procedure may comprise a first container including a neck defining an opening and a body portion, the first container configured to contain a fluid, an elastomeric sealing member including a first end having a first outer diameter, a second end having a second outer diameter less than the first outer diameter, and a first lumen extending therethrough and having an inner diameter that tapers from the second end to the first end, the elastomeric sealing member configured to be disposed within the opening of the neck of the first container, a rigid compression member including a first end, a second end, and a second lumen extending therethrough, the rigid compression member disposed within the first lumen of the elastomeric sealing member, a first fluid supply tube including a first end, a second end, and a third lumen extending therethrough, wherein the third lumen is in fluid communication with the first container, the first end is coupled to the second end of the rigid compression member, and the second end of the first fluid supply tube is positioned external to the first container, a branched connector positioned in line with the first fluid supply tube between the first and second ends thereof, the branched connector including a first fluid inlet, a first fluid outlet, and a second fluid outlet, a portion of the third lumen of the first fluid supply tube extending between the first fluid inlet and the first fluid outlet, a second container configured to contain a fluid, the second container having a second fluid inlet in selective fluid communication with the second fluid outlet of the branched connector, a second fluid supply tube including a first end, a second end, and a fourth lumen extending therethrough, wherein the fourth lumen is in selective fluid communication with a bottom portion of the second container and the second end of the second fluid supply tube is positioned external to the second container, and a first gas supply tube including a first end, a second end, and a fifth lumen extending therethrough, wherein the fifth lumen is in operative fluid communication with the second container and the second end of the first gas supply tube is positioned external to the second container.

Alternatively or additionally to any of the examples above, in another example, an outer surface of the rigid compression member may be configured to threadably engage the first lumen of the elastomeric sealing member.

Alternatively or additionally to any of the examples above, in another example, a third outer diameter of the rigid compression member may be greater than the inner diameter of the first lumen of the elastomeric sealing member along at least a portion of a length of the rigid compression member.

Alternatively or additionally to any of the examples above, in another example, the container and tube set may further comprise a vent hole extending from the first end to the second end of the elastomeric sealing member and a hydrophobic filter disposed within the vent hole.

In another example, a container and tube set arranged and configured to couple to an endoscope for use in an endoscopic procedure may comprise a first container including a neck defining an opening and a body portion, the first container configured to contain a fluid, an elastomeric sealing member including a first end, a second end, and a first lumen extending therethrough, the elastomeric sealing member configured to be disposed adjacent to the opening of the neck of the first container, a rigid compression member including a first end, a second end, and a second lumen extending therethrough, the rigid compression member disposed within the first lumen of the elastomeric sealing member, the first end of the rigid compression member positioned distal to the first end of the elastomeric sealing member and the second end of the rigid compression member positioned proximal to the second end of the elastomeric sealing member, an actuatable member coupled to the rigid compression member, wherein actuation of the actuatable member from a first position to a second position is configured to compress and radially expand the elastomeric sealing member and actuation of the actuatable member from the second position to the first position is configured to release and radially contract the elastomeric sealing member, a first fluid supply tube including a first end, a second end, and a third lumen extending therethrough, wherein the third lumen is in fluid communication with the first container, the first end is coupled to the second end of the rigid compression member, and the second end of the first fluid supply tube is positioned external to the first container, a branched connector positioned in line with the first fluid supply tube between the first and second ends thereof, the branched connector including a first fluid inlet, a first fluid outlet, and a second fluid outlet, a portion of the third lumen of the first fluid supply tube extending between the first fluid inlet and the first fluid outlet, a second container configured to contain a fluid, the second container having a second fluid inlet in selective fluid communication with the second fluid outlet of the branched connector, a second fluid supply tube including a first end, a second end, and a fourth lumen extending therethrough, wherein the fourth lumen is in selective fluid communication with a bottom portion of the second container and the second end of the second fluid supply tube is positioned external to the second container, and a first gas supply tube including a first end, a second end, and a fifth lumen extending therethrough, wherein the fifth lumen is in operative fluid communication with the second container and the second end of the first gas supply tube is positioned external to the second container.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
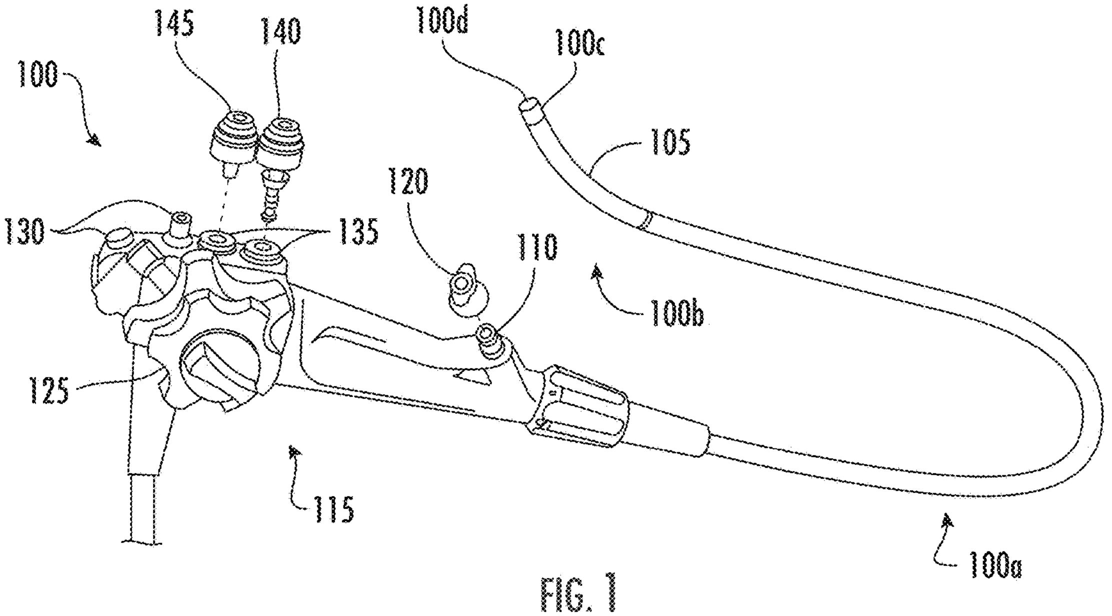
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Embodiments of the present disclosure are described with specific reference to a bottle (e.g., container, reservoir, or the like) and tube assembly or set. It should be appreciated that such embodiments may be used to supply fluid and/or gas to an endoscope, for a variety of different purposes, including, for example to facilitate insufflation of a patient, lens washing, and/or to irrigate a working channel to aid in flushing/suctioning debris during an endoscopic procedure.

Although the present disclosure includes descriptions of a container and tube set suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. Some systems may use two separate water bottles for irrigation and lens wash while other systems may use a single water bottle for both irrigation and lens wash. As clinicians work through each case, some volume of water is depleted from the water bottle and bottles may need to be replaced one or more times over the course of the day. The process of exchanging bottles may require the user to bend or stoop down, remove the cap and associated inlet tubes from the empty bottle, and place them into a full bottle of sterile water without touching/contaminating the tubes against the external bottle or other non-sterile surfaces (e.g., so as not to create an infection risk to the patient). This may be especially difficult in the single bottle devices where multiple inlet hoses dangle from the cap when removing the cap to replace the sterile water bottle.

Additionally, having the sterile water bottles stowed on lower shelves of the carts, alongside the peristaltic pump, and other equipment may make these difficult to visualize and often, the clinician may not realize that the bottle is nearing empty until they are no longer able to deliver irrigation or lens wash to through the distal end of the scope. There is also an inherent risk associated with stowing the water bottles adjacent to the endoscope control boxes. For example, if the water bottle fails in some way (e.g., leak, burst, rupture, etc.) there may be a high risk of water running or spraying onto these high-cost control systems resulting in significant damage or destruction. Disclosed herein are containers and tube sets that are easily viewed by the clinician and reduces the risk of contamination to the tubes when the container is replaced.

Figure 2:
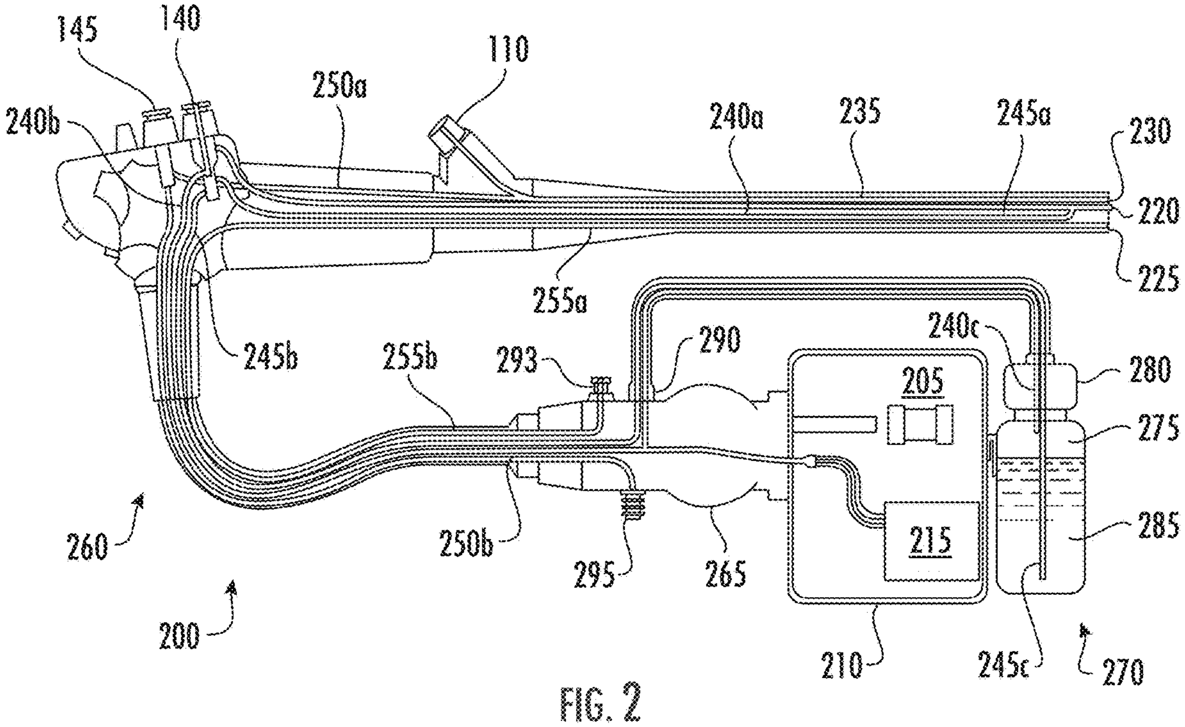
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100*a* that is inserted into a patient. A light source 205 feeds illumination light to a distal portion 100*b* of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100*a* may include a distal tip 100*c* provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 extends along the shaft 100*a* to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240*a* and a lens wash supply line 245*a* run distally from the gas/water valve 140 along the shaft 100*a* and converge at the distal tip 100*c* proximal to the gas/wash nozzle 220 (FIG. 2). The other valve well 135 receives a suction valve 145 for operating a suction operation. A suction supply line 250*a* runs distally from the suction valve 145 along the shaft 100*a* to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260.

A water reservoir or container 270 (e.g., water bottle) is fluidly connected to the endoscope 100 through the connector portion 265 and the umbilical 260. A length of gas supply tubing 240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240*c*. The gas feed line 240*b* from the umbilical 260 branches in the connector portion 265 to fluidly communicate with the gas supply tubing 240*c* at the detachable gas/lens wash connection 290, as well as the air pump 215. A length of lens wash tubing 245*c*, with one end positioned at the bottom of the reservoir 270, passes through the top 280 of the reservoir 270 to the same detachable connection 290 as the gas supply tubing 240*c* on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255*b* in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100. The detachable suction connection 295 may be detachable from the connector portion 265 and/or the suction feed line 250*b* and/or the vacuum source.

The gas feed line 240*b* and lens wash feed line 245*b* are fluidly connected to the valve well 135 for the gas/water valve 140 and configured such that operation of the gas/water valve 140 in the well controls supply of gas or lens wash to the distal tip 100*c* of the endoscope 100. The suction feed line 250*b* is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connector portion 265 and branched to the gas/water valve 140 on the operating handle 115 through the gas feed line 240*b* in the umbilical 260, as well as through the gas supply tubing 240*c* to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240*a* and out the distal tip 100*c* of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245*c*, through the connector portion 265, umbilical 260, through the gas/water valve 140 and down the lens wash supply line 245*a*, converging with the gas supply line 240*a* prior to exiting the distal tip 100*c* of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245*c*, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240*c* to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255*b* in the umbilical 260 and the irrigation supply line 255*a* endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255*b* in the umbilical, and down the irrigation supply line in the shaft 100*a* of the endoscope to the distal tip 100*c*. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245*c*, may be placed in the path of the irrigation supply tubing to help prevent back-flow into the reservoir after water has passed the valve.

FIGS. 3A-3D are schematic drawings illustrating the operation of an embodiment of a hybrid system 300 where the supply tubing for irrigation and lens wash are connected to and drawn from a single water reservoir. It is contemplated that fluids other than water may be used, such as, but not limited to saline. The hybrid system 300 includes the single water reservoir 305, a cap 310 for the reservoir, gas supply tubing 240*c*, lens wash supply tubing 245*c*, irrigation pump 315 with foot switch 318, upstream supply tubing for irrigation 320 and downstream irrigation supply tubing 255*c*. The cap 310 may be configured to attach in a seal-tight manner to the water reservoir 305 by a typically threaded arrangement. The cap 310 may include a gasket to seal the cap 310 to the reservoir 305. The gasket can be an O-ring, flange, collar, and/or the like and can be formed of any suitable material. A number of through-openings (325*a*, 325*b*, 325*c*) in the cap 310 are provided to receive, respectively, the gas supply tubing 240*c*, lens wash supply tubing 245*c*, and upstream irrigation supply tubing 320. In FIGS. 3A-3D, the system depicted includes separate tubing for gas supply, lens wash, and irrigation.

In other embodiments, the gas supply tubing 240*c* and lens wash tubing 245*c* may be combined in a coaxial arrangement. Some illustrative coaxial arrangements are described in commonly assigned U.S. patent application Ser. No. 17/558,239, titled INTEGRATED CONTAINER AND TUBE SET FOR FLUID DELIVERY WITH AN ENDOSCOPE and U.S. patent application Ser. No. 17/558,256, titled TUBING ASSEMBLIES AND METHODS FOR FLUID DELIVERY, the disclosures of which are hereby incorporated by reference. For example, the gas supply tubing may define a lumen that is sufficiently large in diameter to encompass a smaller diameter lens wash tubing, coaxially received within the gas supply tubing, as well as provide air to the water source in an annular space surrounding the lens wash tubing to pressurize the water reservoir (see, e.g., gas and lens wash supply tubing 240*c*, 245*c*). The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2).

In various embodiments, different configurations of valving (not shown) may be incorporated into various embodiments disclosed hereby, including the tubing of the system 200, 300. For example, an in-flow check valve can be disposed in the path of the gas supply tubing 240*c* to help prevent backflow into the air pump 215. In this manner, pressure building within the water reservoir 305 creates a pressure difference between the water source and the gas supply tubing 240*c* helping to maintain a positive pressure in the water source even when large amounts of water may be removed from the water source during the irrigation function. This arrangement compensates for any time lag in air being delivered from the air pump 215 to the water reservoir 305, which might otherwise cause a negative pressure vacuum in the water reservoir. Similarly, an outflow check valve, such as the one-way valve with inlet/outlets and valve insert, may be incorporated in the lens wash supply tubing 245*c*, upstream irrigation supply tubing 320, and/or downstream irrigation supply tubing 255*c* to help prevent backflow of water from either or both of the lens wash and supply tubing for irrigation in the event of a negative pressure situation, as described.

More generally, in many embodiments, a check valve may refer to any type of configuration for fluid to flow only in one direction in a passive manner. For example, a check valve may include, or refer to, one or more of a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, a flow check. Accordingly, a check valve as used herein is meant to be separate and distinct from an active valve that is operated in a binary manner as an on/off valve or switch to allowed flow to be turned on or allow flow to be turned off (e.g., a stop cock valve, solenoid valve, peristaltic pump).

During operation of the system of FIGS. 3A-3D, a flow of water for irrigation may be achieved by operating the irrigation pump 315. A flow of water for lens wash may be achieved by depressing the gas/water valve 140 on the operating handle 115 of the endoscope 100. These functions may be performed independent of one another or simultaneously. When operating lens wash and irrigation at the same time, as fluid is removed from the water reservoir 305, the pressure in the system may be controlled to maintain the lens wash supply tubing 245*c* at substantially the pressure necessary to accomplish a lower flow rate lens wash, while compensating for reduced pressure in the water reservoir 305 due to supplying a high flow rate irrigation. When pressure is reduced in the water reservoir by use of the lens wash function, the irrigation function, or both functions simultaneously, the reduced pressure may be compensated for by the air pump 215 via the gas supply tubing 240*c*.

Figure 3A:
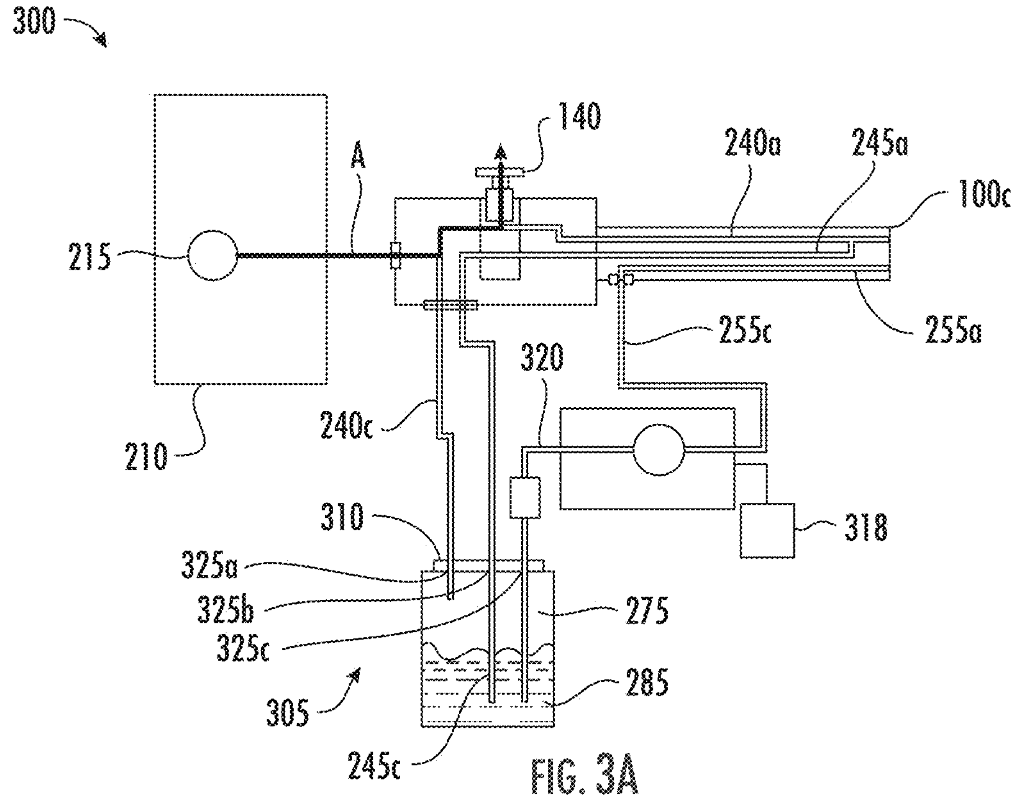
FIG. 3A depicts an endoscope system with endoscope, light source, water reservoir, and tubing assembly for hybrid air, lens wash and irrigation fluid delivery, wherein the system is activated to deliver air to atmosphere.

The schematic set-up in FIGS. 3A-3D has been highlighted to show the different flow paths possible with the hybrid system 300 having supply tubing for irrigation 320 and lens wash supply tubing 245*c* connected to and drawn from the single water reservoir 305. As shown in FIG. 3A, the endoscope 100 is in a neutral state with the gas/water valve 140 in an open position. The neutral state delivers neither gas, nor lens wash, to the distal tip of the endoscope. Rather gas (pressure) is delivered along path A from the pressurizing air pump 215 and vented through the gas feed line 240*b* in the umbilical 260 via the connector portion 265 and through the gas/water valve to atmosphere. Since the system is open at the vent hole in the gas/water valve 140, there is no build up to pressurize the water reservoir 305 and consequently no water is pushed through the lens wash supply tubing 245*c*.

Figure 3B:
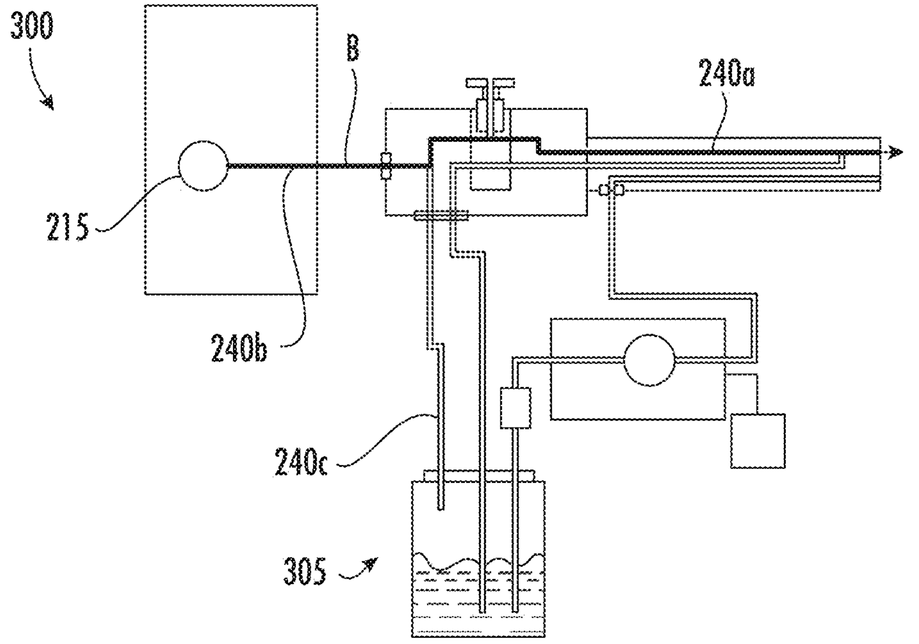
FIG. 3B depicts the endoscope system of FIG. 3A, wherein the system is activated to deliver air to a patient through the patient end of the endoscope.

As shown in FIG. 3B, the endoscope 100 is in a gas delivery state with the gas/water valve 140 in a first position. When gas is called for at the distal tip 100*c*, for example, to clean the end face 100*d* of the distal tip or insufflate the patient body in the treatment area, the user closes off the vent hole in the gas/water valve 140 with a thumb, finger, or the like (first position). In this state, gas (pressure) is delivered along path B from the air pump 215 and flowed through the gas feed line 240*b* in the umbilical 260 via the connector portion 265. The gas continues through the gas/water valve 140 to the gas supply line 240*a* in the endoscope shaft 100*a* and out the gas/lens wash nozzle 220 at the distal tip 100*c*. There is no build up to pressurize the water reservoir since the system is open at the gas/lens water nozzle 220, and consequently no water is pushed through the lens wash supply tubing 245*c*.

Figure 3C:
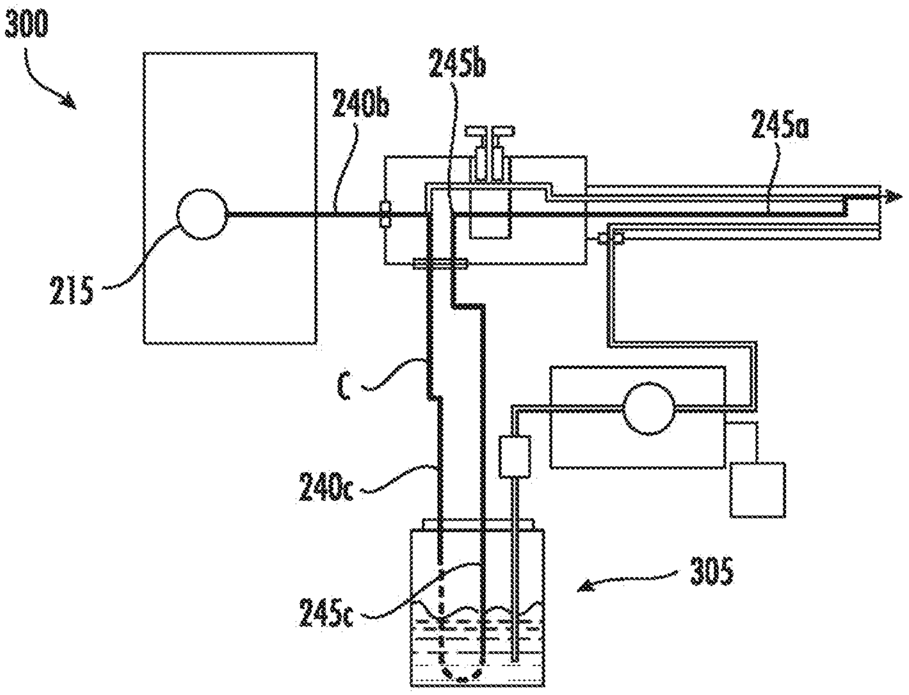
FIG. 3C depicts the endoscope system of FIG. 3A, wherein the system is activated to deliver lens wash fluid through the patient end of the endoscope.

As shown in FIG. 3C, the endoscope 100 is in a lens wash delivery state with the gas/water valve 140 in a second position. When lens wash is called for at the distal tip 100*c*, for example, to clean the end face 100*d* of the distal tip 100*c*, the user, keeping the vent hole in the air/water valve closed off, depresses the valve 140 to its furthest point in the valve well 135. The second position blocks off the gas supply to both atmosphere and the gas supply line 240*a* in the endoscope, and opens up the gas/water valve 140 to allow lens wash water to pass through to the lens wash supply line 245*a* in the endoscope shaft 100*a* and out the gas/lens wash nozzle 220 at the distal tip 100*c*. In this state, gas (pressure) is delivered along path C from the air pump 215, through the branched line in the connector portion 265 and out of the gas supply tubing 240*c* to the water reservoir 305. The gas (pressure) pressurizes the surface of the remaining water 285 in the reservoir 305 and pushes water up the lens wash supply tube 245*c* to the connector portion 265. The pressurized lens wash water is pushed further through the lens wash feed line 245*b* in the umbilical 260 and through the gas/water valve 140. Since the system 300 is closed, gas pressure is allowed to build and maintain a calibrated pressure level in the water reservoir 305, rather than venting to atmosphere or being delivered to the patient. This pressure, along with the endoscope feed and supply lines and external tubing, translates to a certain range of flow rate of the lens wash.

Figure 3D:
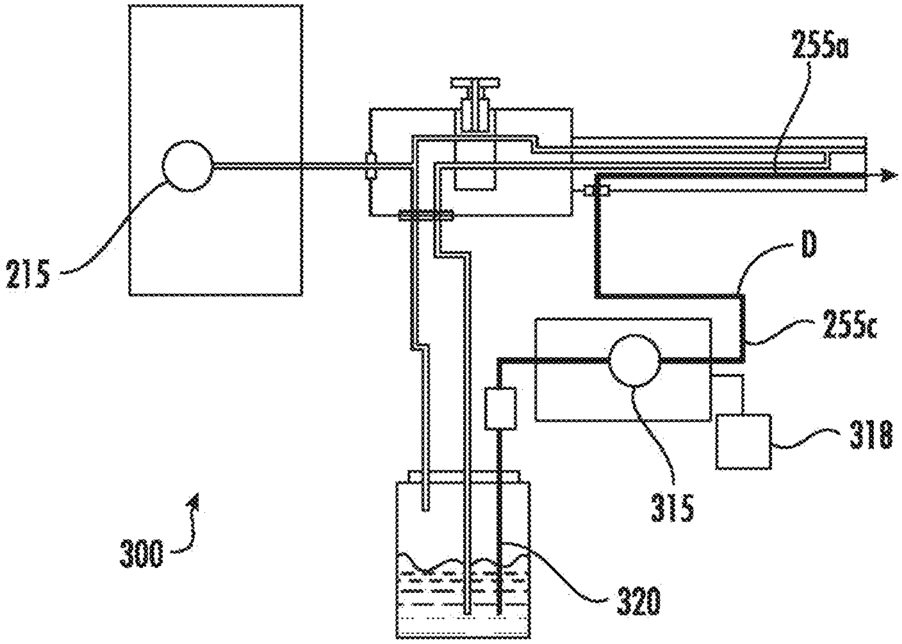
FIG. 3D depicts the endoscope system of FIG. 3A, wherein the system is activated to deliver irrigation fluid through the patient end of the endoscope.

As shown in FIG. 3D, the endoscope 100 is in an irrigation delivery state. This may be performed at the same or a different time from the delivery of gas and/or lens wash. When irrigation is called for at the distal tip 100*c*, for example, if visibility in the treatment area is poor or blocked by debris, or the like, the user activates the irrigation pump 315 (e.g., by depressing foot switch 318) to deliver water along path D. With the pump 315 activated, water is sucked out of the water reservoir 305 through the upstream irrigation supply tubing 320 and pumped along the downstream irrigation supply tubing 255*c* to the connector portion 265. The irrigation pump head pressure pushes the irrigation water further through the irrigation feed line 255*b* in the umbilical 260, through the irrigation supply line 255*a* in the endoscope shaft 100*a*, and out the irrigation opening 225 at the distal tip 100*c*. The irrigation pump pressure may be calibrated, along with the endoscope irrigation feed and supply lines and external tubing, to deliver a certain range of flow rate of the irrigation fluid.

Figure 4:
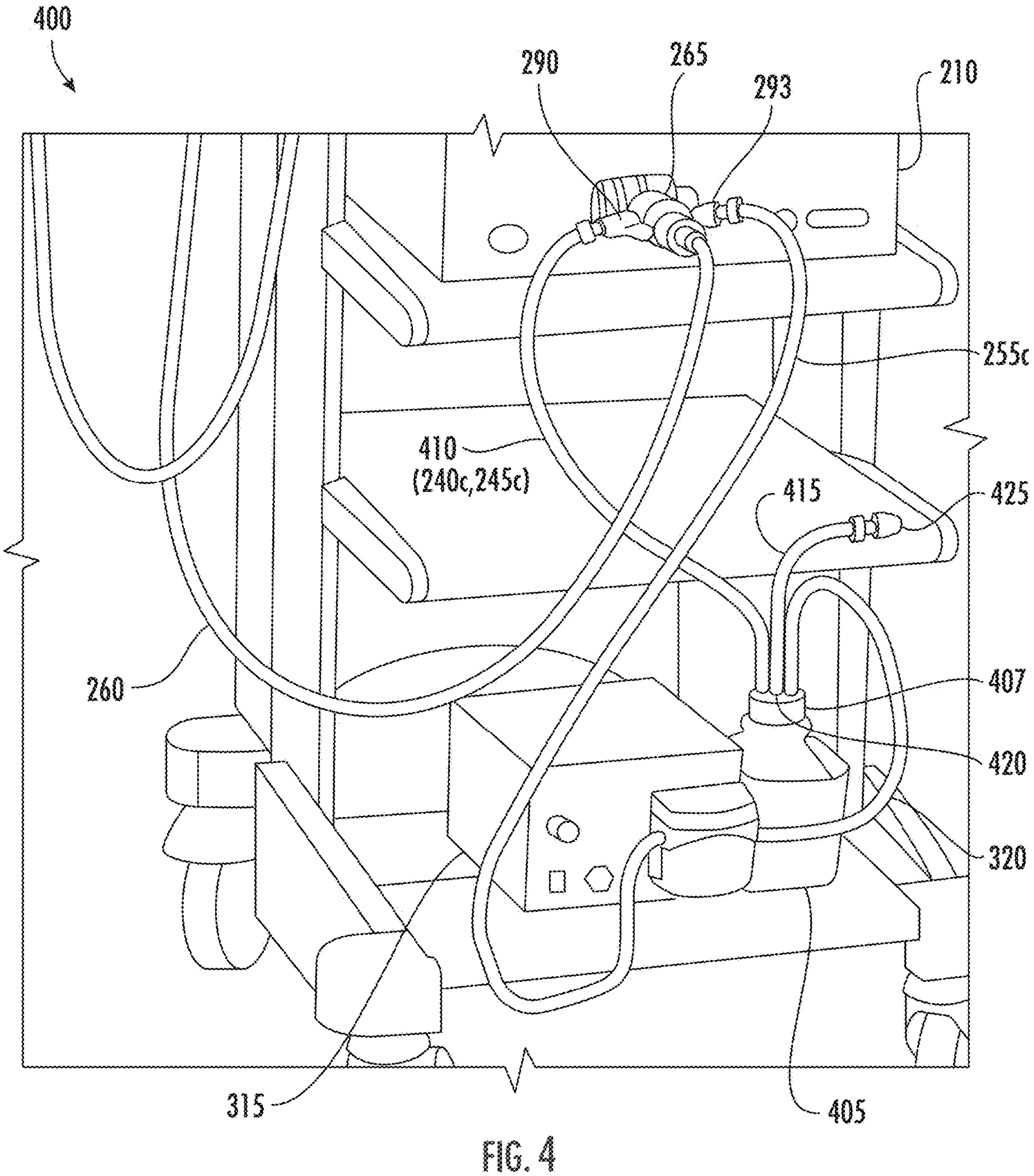
FIG. 4 depicts a hybrid endoscope system including a video processing unit, connector portion, peristaltic irrigation pump, water reservoir and top, coaxial gas and lens wash supply tubing, upstream and downstream irrigation supply tubing, and alternative gas supply tubing.

FIG. 4 is a schematic drawing illustrating a further embodiment of a hybrid system 400 including a video processing unit 210, connector portion 265, peristaltic irrigation pump 315, water reservoir 405 and top 407, coaxial gas and lens wash supply tubing 410, upstream and downstream irrigation supply tubing 320, 255*c*, respectively, and alternative gas (e.g., $CO_2$) supply tubing 415. A length of the alternative gas supply tubing 415 passes from one end positioned in the gas gap 275 (see FIG. 2) between the top 407 of the water reservoir 405 and the remaining water 285 in the reservoir through an additional opening 420 in the top of the reservoir to a detachable connection 425 for a source of the alternative gas supply (e.g., $CO_2$ hospital house gas source). When the alternative gas supply is desired, such as $CO_2$ gas, the air pump 215 on the video processing unit 210 may be turned off and $CO_2$ gas, rather than air, is thereby flowed to the water reservoir 405 pressurizing the water surface. Generally, the flow of $CO_2$ through the endoscope 100 is similar to the flow of air. In the neutral state, $CO_2$ gas flows backward up the gas supply tubing 240*c* to the connector portion 265, up the gas feed line 240*b*, and is vented through the gas/water valve 140 to atmosphere. In the first position, the user closes off the vent hole in the gas/water valve 140, and the $CO_2$ gas is flowed through the gas/water valve to the gas supply line 240*a* in the endoscope shaft 100*a* and out the gas/lens wash nozzle 220 at the distal tip 100*c*. In the second position, the user depresses the valve 140 to the bottom of the valve well 135, keeping the vent hole in the gas/water valve closed off. The second position blocks the $CO_2$ gas supply to both atmosphere and the gas supply line 240*a* in the endoscope 100, and opens up the gas/water valve 140 to allow lens wash water to pass through to the lens wash supply line 245*a* in the endoscope shaft 100*a* and out the gas/lens wash nozzle 220 at the distal tip 100*c*. Gas (pressure) in the reservoir 405 is maintained by delivering gas through alternative gas (e.g., $CO_2$) supply tubing 415. The irrigation function may be accomplished in a similar manner as the operation described above with respect to FIG. 3D.

Figure 5:
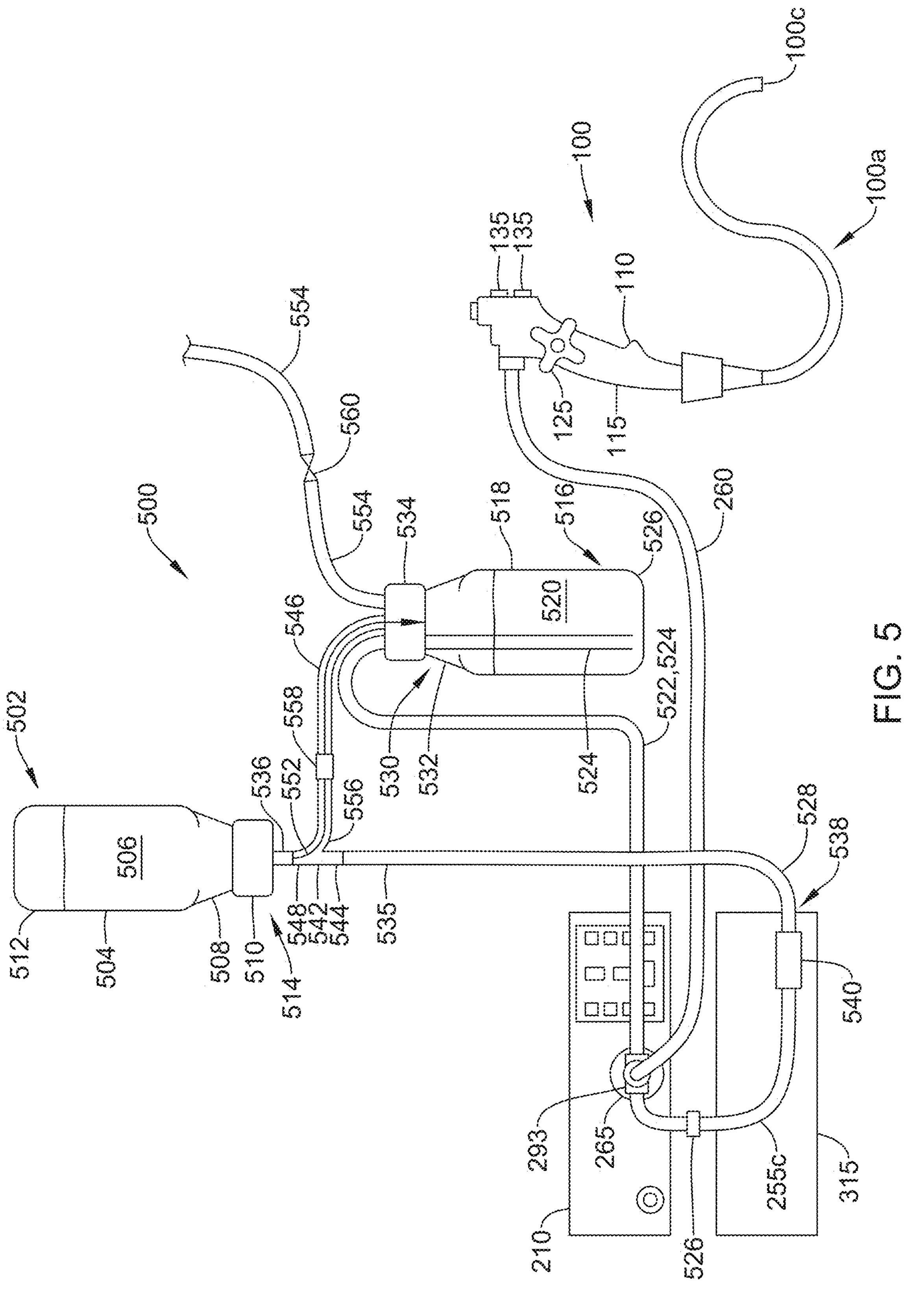
FIG. 5 depicts another illustrative endoscope system having an alternative irrigation fluid supply container.

As described above, it may be desirable to reduce opportunities for contamination to the tube set 240*c*, 245*c*, 320, 410, 415 during replacement of the water reservoir(s). FIG. 5 depicts a schematic view of an illustrative endoscopic system 500 which may reduce the number of water reservoir changes and/or reduce opportunities for contamination during replacement of the water reservoir(s). The system 500 may include components similar to the endoscope and endoscope systems described with regard to FIGS. 1-4; however, not all features may be described or shown here.

FIG. 5 depicts an illustrative system 500 that may include a number of advantages over the current bottle system described above. Generally, the system 500 may include a first reservoir 502 and a second reservoir 516. The first reservoir 502 may be configured to supply water or fluid for both irrigation (e.g., via the first reservoir 502) and lens wash (e.g., via the second reservoir 516). This may allow a single fluid source to be used to provide fluid for both irrigation and lens wash. However, this is not required. In some embodiments, separate reservoirs may individually supply fluid for irrigation and lens wash. While not explicitly shown, the reservoirs 502, 516 may include printed lines, numbers, or other visual indicia to allow a user to easily determine how much fluid is left in the reservoirs 502, 516.

The first reservoir 502 may include a first container 504 configured to hold a first volume of fluid 506. In the illustrated embodiment, the first container 504 is fluidly coupled to the upstream irrigation supply tubing 528 and is configured to provide fluid for irrigation to the endoscope 100. Generally, the irrigation supply tubing 528 may be a water or fluid supply line or tube for supplying water or other fluid to an endoscope. Additionally, the first container 504 may be selectively fluidly coupled to a second fluid reservoir 516. The second reservoir 516 may include a second container 518 configured to hold a second volume of fluid 520. In the illustrated embodiment, the second container 518 is fluidly coupled to the gas and lens wash supply tubing 522, 524 and is configured to provide fluid for lens wash to the endoscope 100. Generally, the lens wash supply tubing 524 may be a water or fluid supply line or tube for supplying water or other fluid to an endoscope. The gas and lens wash supply tubing 522, 524 may be coaxially arranged. For example, the gas supply tubing 522 may define a lumen that is sufficiently large in diameter to encompass a smaller diameter lens wash tubing 524, coaxially received within the gas supply tubing, as well as provide air to the water source in an annular space surrounding the lens wash tubing to pressurize the second reservoir 516. The lens wash supply tubing 524 may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion 265. In other embodiments, the gas and lens wash supply tubing 522, 524 may be arranged in a side-by-side arrangement.

The first container 504 may be a rigid bottle extending from a closed first end 512 to a second end 514 defining an opening (not explicitly shown). The first end 512 may have a first diameter and the second end 514 may have a reduced diameter neck region 508. For example, the diameter of the neck region 508 may be less than the diameter of the first end 512. A removable cap or seal 510 configured to form a fluid tight seal with the opening at the second end 514 may be removably coupled thereto. The removable cap 510 may be coupled to the second end region 514 using a number of different techniques. For example, the cap may be coupled to the second end region 514 using a threaded engagement, a friction fit, a snap fit, etc.

In the illustrated embodiment, the first container 504 may be inverted from a typical orientation. For example, typically a rigid bottle may be placed on a level surface with the closed first end 512 resting thereon and the second end 514 defining the opening pointed upwards. In contrast, in the illustrated embodiment, the second end 514 may be pointed downwards. This may allow gravity to draw the fluid 506 towards the second end 514 which may reduce or eliminate the need for tube sets which reach to the first end 512 of the first container 504. Said differently, such an arrangement allows for fluid 506 to flow without the need for a pickup tube to travel through the cap 510 to the bottom (first end 512) of the first container 504 thus reducing possible cross contamination. It is contemplated that a fluid supply tube 536 may be coupled to the cap 510 and/or the first container 504 in a number of different manners, as will be described in more detail herein. In some embodiments, the fluid supply tube 536 may be the first end of the irrigation supply tubing 528. It is contemplated that the fluid supply tube 536 may be separate tubular member from the irrigation supply tubing 528 or may be formed as a single monolithic structure therewith.

The first reservoir 502 to be positioned on a detachable elevated connection configured to maintain the first container 504 in the inverted orientation. Elevating the first reservoir 502 may allow the first reservoir 502 to be positioned above the level of an endoscope cart which may enable the user to see the fluid 506 level at any time. This may help the clinician avoid running out of fluid during a procedure. Additionally, elevating the reservoir may eliminate the need for the clinician to bend or stoop during setup of the system 500 and/or to change the first reservoir 502. In some cases, head pressure generated from the elevating the first reservoir 502 may enable rapid priming of the irrigation circuit (and/or lens wash circuit if so connected) which may save time during setup. It is further contemplated that elevating the first reservoir 502 may allow the first reservoir 502 to be positioned away from expensive capital equipment thus reducing or eliminating the potential for fluid running or flowing inadvertently onto the capital equipment and causing damage or destruction.

The second container 518 may be a rigid bottle extending from a closed first or bottom end 526 to a second or top end 530 defining an opening (not explicitly shown). The first end 526 may have a first diameter and the second end 530 may have a reduced diameter neck region 532. For example, the diameter of the neck region 532 may be less than the diameter of the first end 526. A removable cap or seal 534 configured to form a fluid tight seal with the opening at the second end 530 may be removably coupled thereto. The removable cap 534 may be coupled to the second end region 530 using a number of different techniques. For example, the cap may be coupled to the second end region 530 using a threaded engagement, a friction fit, a snap fit, etc.

In some embodiments, the first and second containers 504, 518 may be entirely translucent, entirely opaque, or combinations thereof. The volume of the first and second containers 504, 518 may be variable. For example, the volume of the first and second containers 504, 518 may be 500 milliliters (mL) or greater, 1000 mL or greater, 2000 mL or greater, 3000 mL, 4000 mL or greater, etc. The volume may be less than 500 mL or greater than 4000 mL, as desired. One or both of the first and second reservoirs 502, 516 may be pre-filled (e.g., prior to entering the procedure suite or at the time of manufacturing) with water or other fluid. In some cases, the clinician may select the reservoir(s) 502, 516 from a plurality of differently sized available reservoirs based on the number and/or types of procedures expected for a day. In the illustrated embodiments, the first reservoir 502 may supply fluid to the second reservoir 516. By selecting a first reservoir 502 having a volume large enough to accommodate an entire day of procedures, the need for replacing the sterile fluid source (e.g., the first reservoir 502) may be reduced or eliminated. In some cases, the first reservoir 502 may be used to periodically refill the second reservoir 516. Thus, the volume of the first reservoir 502 may be greater than the volume of the second reservoir 516, although this is not required. It is further contemplated that, in some embodiments, one or both of the first or second reservoirs 502, 516 may be formed from one or more layers of a lightweight, flexible material, such as, but not limited to, low density polyethylene (LDPE), thermoplastic polyurethane (TPU), silicone, polyethylene terephthalate (PET), aluminum, nylon, polyethylene (PE), plasticized polyvinyl chloride (PVC), or combinations thereof, etc. In some cases, the first and/or second containers 504, 518 may be a flexible bag analogous to those utilized to deliver intravenous replacement fluid in clinical settings (for example, an intravenous (IV) fluid bag).

The first reservoir 502 may be connected in fluid communication with a lumen of the upstream irrigation supply tube 528. The upstream irrigation supply tube 528 extends from a second end region 538 external to the first container 504 and positioned within a pump head 540 of the peristaltic irrigation pump 315 to a first end 535. The first end 535 of the upstream irrigation supply tube 528 is coupled to the first container 504 with the lumen of the upstream irrigation supply tube 528 in fluid communication with the interior of the first container 504. In some cases, the first end 535 of the upstream irrigation supply tube 528 may be connected to the first container 504 via a branched connector 542. The second end of the upstream irrigation supply tube 528 is configured to be fluidly coupled with an irrigation lumen of the endoscope 100. When irrigation water is required, fluid is pumped from the first container 504 by operating the irrigation pump 315, such as by depressing a footswitch (not shown), and flows from the first reservoir 502, through the upstream irrigation supply tubing 528 and a branched connector 542, through the downstream irrigation supply tubing 255*c*, through the irrigation connection 293, through the irrigation feed line 255*b* in the umbilical 260, and down the irrigation supply line 255*a* in the shaft 100*a* of the endoscope to the distal tip 100*c*.

The downstream irrigation supply tubing 255*c* may include a loaded check valve or flow control valve 550 positioned in line with the downstream irrigation supply tubing 255*c*. The flow control valve 550 may prevent the unintentional flow of fluid from the first container 504 to the endoscope 100. In some cases, the flow control valve 550 may be configured to open when the pressure within the downstream irrigation supply line 255*c* reaches a predetermined minimum pressure. It is contemplated that the predetermined minimum pressure may be greater than the head pressure created by the height differential between the first reservoir 502 and the irrigation pump 315. The flow control valve 550 may also prevent fluid from leaking from the downstream irrigation supply tube 255*c* when the endoscope 100 is changed between patients and the tubing set connector is separated from the endoscope water port.

As described above, the second reservoir 516 may include a cap 534 releasably coupled to the second end region 530 thereof. The cap 534 may include a plurality of openings or ports to allow a plurality of tubes to be in fluid communication with an interior of the second container 518. The cap 534 may include openings for a second fluid supply tube 546, the gas and lens wash supply tubing 522, 524, and an alternative gas supply tubing 554.

The second reservoir 516 may be connected in fluid communication with a gas supply tubing 522 and/or an alternate gas supply tubing 554 and a lens wash supply tubing 524. The gas supply tubing 522 extends from a second end external to the second container 518 through a reservoir opening in the cap 534 adjacent the second end 530 of the second container 518. The gas supply tubing 522 and/or alternate gas supply tubing 554 may terminate within a reservoir gap, at or below the opening, but not extending into the remaining fluid 520 in the second container 518. However, in some cases, the gas supply tubing 522 and/or alternate gas supply tubing 554 may extend into the fluid 520. For example, the gas supply tubing 522 and/or alternate gas supply tubing 554 may terminate within the fluid 520 with gas bubbling up through the fluid 520 to pressurize the second container 518. A lumen extends through the gas supply tubing 522 for receiving a flow of air and/or gas therethrough. Similarly, a lumen extends through the alternate gas supply tubing 554 for receiving a flow of gas therethrough. The lumens of the gas supply tubing 522 and/or the alternate gas supply tubing 554 are in operative fluid communication with a top portion of the container 518. The lens wash supply tubing 524 extends from a second end external to the second reservoir 516 through the reservoir opening in the cap 534, terminating in a first end within the remaining fluid 520 at or substantially adjacent to the first or a bottom end 526 of the second container 518. In some embodiments, the fluid supply tubing 524 may terminate at the opening in the cap 534. A lumen extends through the lens wash supply tubing 524 for receiving a flow of fluid therethrough. The lumen of the lens wash supply 524 is in selective operative fluid communication with the bottom portion of the second container 518. In the illustrated embodiment, the gas supply tubing 522 and the fluid supply tubing 524 may enter the second container 518 through a single or common opening. For example, the gas supply tubing 522 and the lens wash supply tubing 524 may be coaxially arranged. However, this is not required. In some cases, the gas supply tubing 522 and the fluid supply tubing 524 may extend in a side by side arrangement or may be separately connected to the second container 518 in different locations. The opening in the cap 534 may include a seal or O-ring. configured to seal the cap 534 about the tubing 522, 524 in a fluid and pressure tight manner.

The second ends of the gas supply tubing 522 and the lens wash supply tubing 524 may be connected in fluid communication with the endoscope at gas/lens wash connection on the connector portion 265 of the umbilical 260. The gas supply tubing 522 is connected in fluid communication with a gas pump (not explicitly shown) and gas feed line (not explicitly shown), and the lens wash supply tubing 524 is connected in fluid communication with lens wash feed line (not explicitly shown), within connector portion 265.

The second fluid supply tube 546 may be in selective fluid communication with the first reservoir 502. For example, a branched connector 542 may be positioned in-line with the upstream irrigation tubing 528 and/or the first fluid supply tube 536. In some embodiments, the branched connector 542 may be a "Y" connector or a "T" connector having an inlet leg 548 defining a first fluid inlet, a first outlet leg 544 defining a first fluid outlet, and a second outlet leg 556 defining a second fluid outlet. However, it is contemplated that the branched connector 542 may include more than one fluid inlet and fewer than two or more than two fluid outlets, if so desired.

The branched connector 542 may be positioned in-line with the upstream irrigation tubing 528 such that the inlet leg 548 and the first outlet leg 544 are fluidly coupled with the lumen of the upstream irrigation tubing 528. In some examples, a portion of the lumen first fluid supply tube 536 and/or a lumen of the upstream irrigation tubing may extend between the first fluid inlet leg 528 and the first fluid outlet leg 544. Fluid may flow from the first reservoir 502, through the first fluid supply tube 536, through the branched connector 542 and through the upstream irrigation tubing 528. The branched connector 542 may be positioned such that the inlet leg 548 is upstream of the outlet legs 544, 556 relative to a flow of irrigation fluid. In some embodiments, the branched connector 542 and a coupling member for coupling to the cap 510 and/or first container 504 may be molded or formed as a single monolithic structure. It is contemplated that this may reduce connection points in the fluid circuit. In such an instance, the first end 535 of the irrigation supply tubing 528 may be fluidly coupled to the first outlet leg 544 of the branched connector 542.

The second outlet leg 556 may be fluidly coupled to the second fluid supply tube 546 of the second reservoir 516. A flow control mechanism, such as, but not limited to, a one-way valve 558 may be positioned between the second fluid outlet of the second outlet leg 556 and the second fluid supply tube 546 of the second reservoir 516 to selectively fluidly couple the second container 518 with the first container 504. The one-way valve 558 may be configured to be opened to allow fluid to selectively pass from the first reservoir 502 to the second reservoir 516 while preventing fluid (e.g., gas, water, or other fluid) from exiting the second container 518 and entering the irrigation supply tubing 528 and/or the first container 504. In some embodiments, the one-way valve 558 may be replaced with a clamp which may compress the second fluid supply tube 546 to selectively fluidly isolate the second container 518 from the first container 504 and removed to selectively couple the second container 518 with the first container 504. In yet other embodiments, the one-way valve 558 may be replaced with a spring-loaded valve, a stopcock, or other two-way valve. When it is desired to add fluid to the second reservoir 516 from the first reservoir 502, the one-way valve 558 (or other flow control mechanism) may be opened or released. Fluid may then be at least partially diverted from the irrigation supply tubing 528 through the second outlet leg 556 of the branched connector 542 and into the second container 518 along flow path 552. Fluid may be added to the second container 518 while the irrigation pump 315 is running or while the irrigation pump 315 is idle, as desired.

The alternative gas supply tube 554 of the second container 518 may be configured to be coupled to an alternative gas supply (e.g., $CO_2$ hospital house gas source). The alternative gas supply tube 554 may extend from a second end external to the second container 518 to a first end coupled to the second container 518. The alternative gas supply may be used to pressurize the second container 518 to supply lens wash to the endoscope 100 and/or to provide insufflation. A lumen extends through the alternative gas supply tube 554 for receiving a flow of gas therethrough. The lumen of the alternative gas supply tube 554 is in operative fluid communication with a top portion of the second container 518. The flow of the $CO_2$ through the system 500 may be similar to that described above. For example, in the neutral state, $CO_2$ gas flows through the alternative gas supply tube 554 into the second container 518, up the gas supply tubing 522 to the connector portion 265, up the gas feed line **240*b* in the umbilical 260, and is vented through the gas/water valve 140 to atmosphere. In the first position, the user closes off the vent hole in the gas/water valve 140, and the $CO_2$ gas is flowed through the alternative gas supply tube 554 into the second container 518, up the gas supply tubing 522 to the connector portion 265, through the gas/water valve to the gas supply line 240*a* in the endoscope shaft 100*a* and out the gas/lens wash nozzle 220 at the distal tip 100*c*. In the second position, the user depresses the valve 140 to the bottom of the valve well 135, keeping the vent hole in the gas/water valve closed off. The second position blocks the $CO_2$ gas supply to both atmosphere and the gas supply line 240*a* in the endoscope 100, and opens up the gas/water valve 140 to allow lens wash water to pass through to the lens wash supply line 245*a* in the endoscope shaft 100*a* and out the gas/lens wash nozzle 220 at the distal tip 100*c*. Gas (pressure) in the second reservoir 516 is maintained by delivering gas through the alternative gas supply tube 554. It is contemplated that the one-way valve 558 is in the closed configuration during delivery of the $CO_2$ gas to allow the container 518 to pressurize. In some instances, the one-way valve 558 may be configured to close without user intervention in response to the delivery of $CO_2$ to the second container 518. In some embodiments, the system 500 may include a branched connector (such as, but not limited to a "Y" or "T" connector) at the alternative gas supply tube 554 to allow either air or $CO_2$ to be used for pressurization or insufflation. It is further contemplated that the alternative gas supply tube 554 may include a pressure relief valve 560, such as, but not limited to, a 3-way stopcock, a clamp, or a spring-loaded valve, to vent pressure within the second container 518 and/or to block a flow of pressurized gas to the second container 518 during refilling of the second container 518**, during procedure change-overs, and/or during equipment change-overs.

As the pressurized second container 518 is fluidly isolated from the first container 504 when the one-way valve 558 is closed, it is contemplated that the clinician may replace the first reservoir 502 with a new (full) reservoir without losing patient insufflation. Loss of patient insufflation may result in a loss of position of the endoscope 100 within the body. In current one or two bottle systems, it may not be possible to replace the water reservoirs without loss of patient insufflation.

If there is a need to replace the first reservoir 502 with a new full reservoir, for example when the first reservoir 502 is empty or near empty, the user may position the new reservoir near the first reservoir 502 to be replaced. The user may then invert the first reservoir 502 such the second end region 514 is pointed up and disengage the cap 510 and/or the first fluid supply tube 536. The cap 510 and/or the first fluid supply tube 536 may then be coupled to the new reservoir. Some illustrative coupling mechanisms between the first fluid supply tube 536 and the cap and/or first reservoir 502 are described with respect to FIGS. 6-11. The reservoir replacement may be performed without requiring the clinician to bend or stoop to access the first reservoir 502. This method of replacing the first reservoir 502 may have a lower risk of introducing contaminants into the systems relative to traditional bottle systems. For example, the change out method described herein may allow the first reservoir 502 to be changed out without having tubing tangling from a cap (as in a bottle system). Further, the system 500 may remain largely closed as the first reservoir 502 is changed out.

Figure 6:
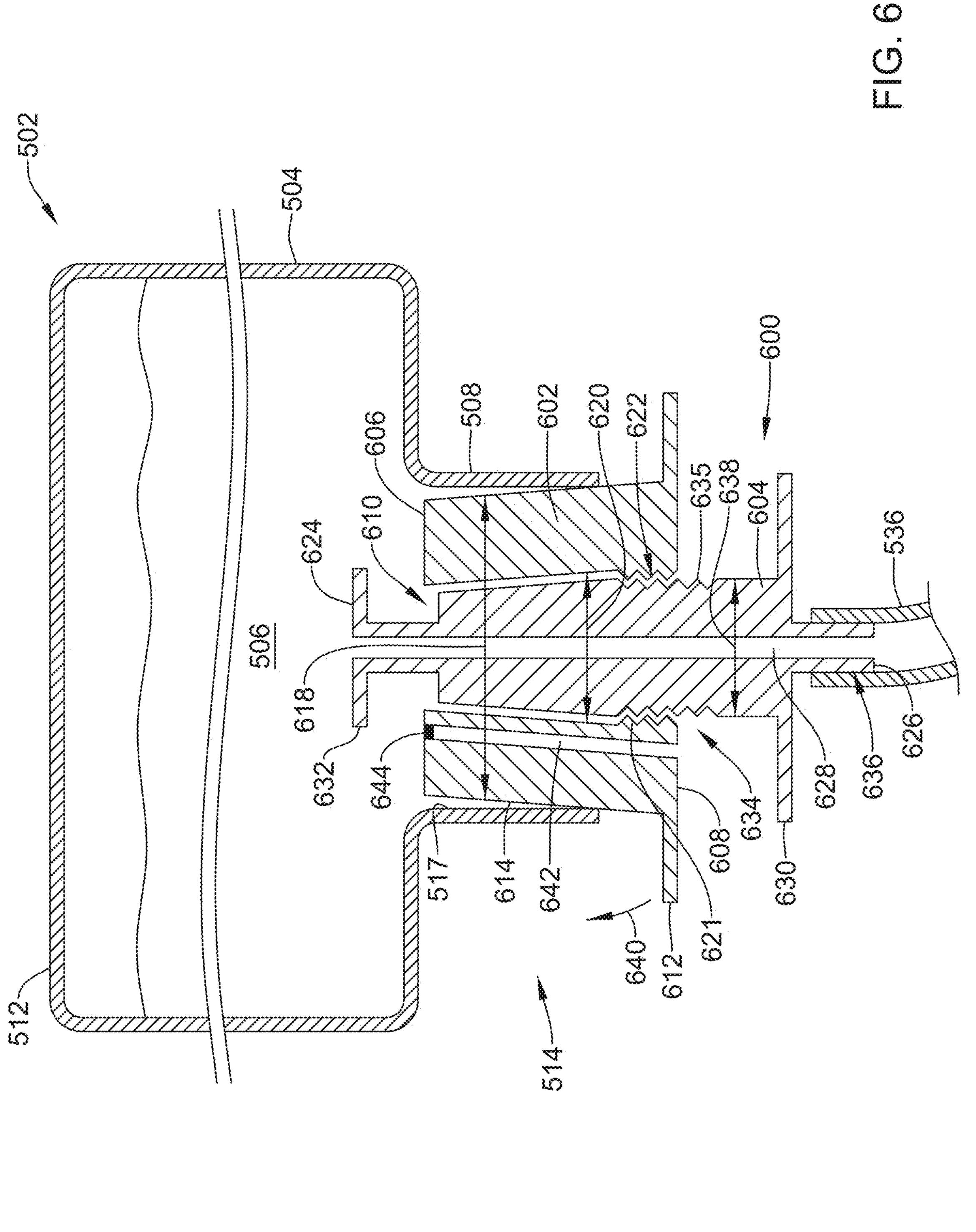
FIG. 6 depicts a schematic cross-sectional view of the first container with an illustrative connection system.

FIG. 6 depicts a schematic cross-sectional view of the first container 504 with an illustrative connection system 600. The connection system 600 may be releasably coupled to the first container 504 such that the connection system 600 may be removed from the first container 504 and coupled with a different container. Generally, the connection system 600 may be positioned at the opening of the first container 504 or within the neck region 508 of the first container 504.

The connection system 600 may include a sealing member 602 and a compression member 604. The sealing member 602 may be at least partially disposed within a cavity of the first container 504 defined by the neck region 508. The sealing member 602 may extend from a first end 606 to a second end 608 with a lumen 610 extending therethrough. The sealing member 602 may be formed from a deformable or elastomeric material, such as, but not limited to, silicone, rubbers, thermoplastic elastomers, or other material that allows the sealing member 602 to temporarily deform. In some embodiments, the sealing member 602 may include one or more radially-outward extending tabs 612 at or adjacent to the second end 608 thereof. It is contemplated that the one or more tabs 612 may be a single continuous tab 612 extending about an entire perimeter of the sealing member 602 or about less than an entire perimeter of the sealing member 602. In some embodiments, the one or more tabs 612 may include two or more tabs spaced about a perimeter of the sealing member 602. When more than one tab 612 is provided, the tabs 612 may be spaced uniformly or eccentrically about the perimeter of the sealing member 602, as desired. The tab(s) 612 may provide a gripping region to allow a user to pull or remove the sealing member 602 from the first container 504.

An outer surface 614 of the sealing member 602 may be configured to contact an inner surface 517 of the first container 504 to form a fluid-tight seal therebetween. In some examples, an outer diameter 618 of the sealing member 602 may taper or decrease along at least a portion of the length thereof. In some examples, the outer diameter 618 may decrease from a location adjacent to the second end 608 to the first end 606. It is contemplated that the tapered outer diameter 618 may facilitate assembly of the sealing member 602 with the first container 504. Further, the tapered outer diameter 618 may allow the sealing member 602 to interface with containers 504 having different internal neck diameters. An outer diameter 618 of the sealing member 602 adjacent to the first end 606 thereof may be less than an inner diameter of the neck region 508 of the first container 504 to allow the first end 606 of the sealing member 602 to be inserted into the neck region 508 with little or no resistance while the outer diameter 618 of the scaling member adjacent to the second end 608 may be greater than an inner diameter of the neck region 508 to limit advancement of the sealing member 602 into the first container 504 and/or to facilitate the formation of a fluid-tight seal with the first container 504. However, in other embodiments the outer diameter 618 of the sealing member 602 may be approximately constant from a location adjacent to the second end 608 to the first end 606.

In some examples, a diameter 620 of the lumen 610 of the sealing member 602 may taper or decrease from the second end 608 to the first end 606. In other examples, the diameter 620 of the lumen 610 may be approximately constant from the first end 606 to the second end 608. It is contemplated that the lumen 610 may be configured to receive at least a portion of the compression member 604 therein. As will be described in more detail herein, the compression member 604 may be configured to bias the sealing member 602 radially outward to facilitate the formation of a fluid-tight seal between the sealing member 602 and the first container 504. A second end region 622 of the lumen 610 may include retention features 621, such as, but not limited to, threads grooves, ridge, tabs, texturing, ribs, etc. configured to engage mating features on an outer surface of the compression member 604 and/or increase frictional engagement with the compression member 604, although this is not required.

The compression member 604 may extend from a first end 624 to a second end 626 with a lumen 628 extending therethrough. The compression member 604 may be formed from a rigid material that allows the compression member 604 to at least temporarily deform the sealing member 602. For example, the compression member 604 may be formed from a metal, an alloy, or a, polymer such as, but not limited to, stainless steel, anodized aluminum, titanium, nylon, acrylic, ultra-high molecular weight polyurethane, polycarbonate, polyvinyl chloride (PVC), etc. In some embodiments, the compression member 604 may include one or more radially-outward extending tabs 630 at or adjacent to the second end 626 thereof. It is contemplated that the one or more tabs 630 may be a single continuous tab 630 extending about an entire perimeter of the compression member 604 or about less than an entire perimeter of the compression member 604. In some embodiments, the one or more tabs 630 may include two or more tabs spaced about a perimeter of the compression member 604. When more than one tab 630 is provided, the tabs 630 may be spaced uniformly or eccentrically about the perimeter of the compression member 604, as desired. The tab(s) 630 may provide a gripping region to allow a user to pull or remove the compression member 604 from the scaling member 602.

In some embodiments, the compression member 604 may include one or more radially-outward extending tabs 632 at or adjacent to the first end 624 thereof. It is contemplated that the one or more tabs 632 may be a single continuous tab 632 extending about an entire perimeter of the compression member 604 or about less than an entire perimeter of the compression member 604. In some embodiments, the one or more tabs 632 may include two or more tabs spaced about a perimeter of the compression member 604. When more than one tab 632 is provided, the tabs 632 may be spaced uniformly or eccentrically about the perimeter of the compression member 604, as desired. The tab(s) 632 may be configured to retain the compression member 604 within the lumen 610 of the sealing member 602. In some examples, the tab(s) 632 may be configured to deflect towards the body of the compression member 604 to allow the compression member 604 to be inserted through the lumen 610 of the sealing member 602. Once the tab(s) 632 have exited the lumen 610 of the sealing member 602 adjacent the first end 606 thereof, the tab(s) 632 may return to their radially-extending configuration. The tab(s) 632 may be configured to contact the first end 606 of the sealing member 602 to prevent unintentional disengagement of the compression member 604 from the sealing member 602.

An outer surface of the compression member 604 along an intermediate region 634 thereof may include retention features 635, such as, but not limited to, threads, grooves, ridges, tabs, texturing, ribs, etc. configured to engage mating retention features 621 on an inner surface of the sealing member 602 and/or increase frictional engagement with the sealing member 602, although this is not required. In some examples, an outer diameter 638 of the compression member 604 may taper or decrease along at least a portion of the length thereof. In some examples, the outer diameter 638 may decrease from a location adjacent to the tab(s) 630 towards the first end 624. It is contemplated that the tapered outer diameter 638 may facilitate assembly of the compression member 604 with the sealing member 602. An outer diameter 638 of the compression member 604 adjacent to the intermediate region 634 thereof may be greater than a diameter 620 of the lumen 610 of the sealing member 602 to allow the compression member 604 to bias the sealing member 602 radially outwards while an outer diameter 638 of the compression member 604 adjacent to the first end 624 thereof may be less than a diameter 620 of the lumen 610 to allow the compression member 604 to be advanced through the lumen 610. However, in other embodiments the outer diameter 638 of the compression member 604 may be approximately constant from a location adjacent to the tab(s) 630 towards the first end 624.

The second end 626 of the compression member 604 may define a port 636 configured to be fluidly coupled with a first end of the first fluid supply tube 536. In some examples, the port 636 may be a hose barb including a plurality of raised ribs configured to be disposed within a lumen of the first fluid supply tube 536 and engage an inner surface thereof. In other examples, the port 636 may be disposed over an outer surface of the first fluid supply tube 536. The port 636 may have an outer diameter that is sized to couple with the first fluid supply tube 536. In some examples, the outer diameter of the port 636 may be less than an outer diameter of the tab(s) 630 or the intermediate region 634 of the compression member 604. However, this is not required.

To assemble the connection system 600 with the first container 504, the first container 504 may be placed in an upright configuration (e.g., with the second end 514 pointed up) and the cap 510 removed. The sealing member 602 may be inserted into the neck region 508 of the first container 504. The compression member 604 may then be inserted into the lumen 610 of the sealing member 602. In some examples, the compression member 604 may be at least partially disposed within the lumen 610 of the sealing member 602 prior to the sealing member 602 being inserted into the neck region 508 of the first container 504. The compression member 604 may be inserted into the lumen 610 adjacent the second end 608 of the scaling member 602 and advanced towards the first end thereof 606. In some cases, the compression member 604 may be advanced through the lumen 610 until the tab(s) 632 exit the first end 606 of the sealing member 602, although this is not required.

As the compression member 604 is advanced within the lumen 610, the outer surface of the compression member 604 may contact the surface of the lumen 610 which may cause the compression member 604 to force the sealing member 602 to expand radially outward or to be biased radially outward against the inner surface 517 of the neck region 508 of the first container 504 and thus creating a sealing interface. It is contemplated that the outer surface of the sealing member 602 may be smooth to create a fluid-tight seal between the sealing member 602 and the first container 504. As described above, the scaling member 602 and/or the compression member 604 may include features which help retain the compression member 604 within the lumen 610 of the sealing member 602. When the connection system 600 is assembled with the first container 504, the lumen 628 of the compression member 604 is in fluid communication with the interior of the first container 504 and thus the fluid 506 in the first container 504. The first container 504 may be inverted to allow fluid 506 to flow through the lumen 628 of the compression member 604 to the first fluid supply tube 536. From the first fluid supply tube 536, the fluid may flow to the upstream irrigation tube 528 or to the second container 518, as described with respect to FIG. 5.

In some embodiments, the connection system 600 may be provided with an air vent 642 that allows air to flow into the first container 504 as fluid is 506 is withdrawn from the first container 504. The air vent 642 may help prevent the first container 504 from collapsing under vacuum and/or prevent a vacuum vapor lock which may prevent or make it more difficult to extract fluid 506 from the first container 504. The air vent 642 may be a passageway extending from the first end 606 to the second end 608 of the sealing member 602 to fluidly connect the interior of the first container 504 with atmosphere. A hydrophobic filter 644 may be positioned at an opening of the air vent 642 or within the passageway thereof to prevent fluid 506 from leaking from the first container 504 while allowing air to enter. Alternatively, or additionally, it is contemplated that the air vent 642 may extend through the compression member 604. In some embodiments, in place of or in addition to the air vent 642, a hole may be punctured into the first end 512 or a sidewall above the water line of the container to allow air to enter the first container 504 as fluid exits. In other examples, the connection system 600 may include a vent tube that extends above the fluid line to the air headspace similar in form and function to the vent tube 840 described with respect to FIG. 8B.

In some examples, it may be desirable to disassemble the connection system 600 from the first container 504 and/or the compression member 604 from the scaling member 602. It is contemplated that the one or more tab(s) 612 of the sealing member 602 may be biased towards the neck region 508, as shown at arrow 640, which may increase the diameter of the lumen 610 and allow the compression member 604 to be released from the sealing member 602. For example, biasing the one or more tab(s) 612 towards the neck region 508 may allow the retention features 621 of the sealing member 602 to moved away from the retention features 635 of the compression member 604 such that the retention features 635 of the compression member 604 are released from the sealing member 602 allowing the compression member 604 to be removed from the scaling member 602. In some examples, the compression member 604 may be rotated to disengage the compression member 604 from the sealing member 602. In another example, the retention features 621, 635 may include threaded sections that are interrupted on at least one of the sealing member 602 and/or compression member 604, such that the user could rotate the compression member 604 relative to the scaling member 602 to an area where the retaining features 621, 635 are not present thus releasing the "lock" between the sealing member 602 and the compression member 604. It is further contemplated that removing the compression member 604 from the sealing member 602 allows the sealing member 602 to return to its unbiased or unexpanded configuration such that the sealing member 602 may be removed from the neck region 508 of the first container 504. In some examples, the compression member 604 need not be entirely removed from the lumen 610 of the sealing member 602 to allow for removal of the connection system 600 from the first container 504.

If the first reservoir 502 needs to be replaced, the first reservoir 502 may be positioned upright (e.g., with the second end 514 pointed up) to avoid or limit leakage or spills. The compression member 604 may be retracted or removed from the sealing member 602 in the manner described herein. Next, the sealing member 602 may be removed from the first container 504. The connection system 600 may then be inserted into a different full reservoir in the manner described herein.

Figure 7A:
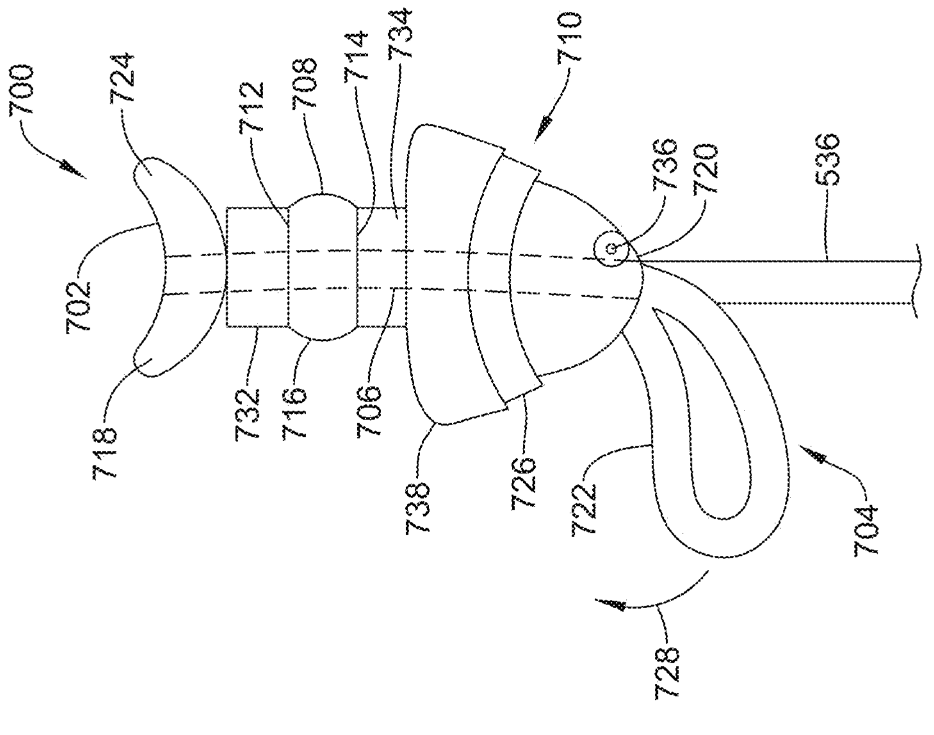
FIG. 7A depicts a perspective view of another illustrative connection system in an insertion or removal configuration.
Figure 7B:
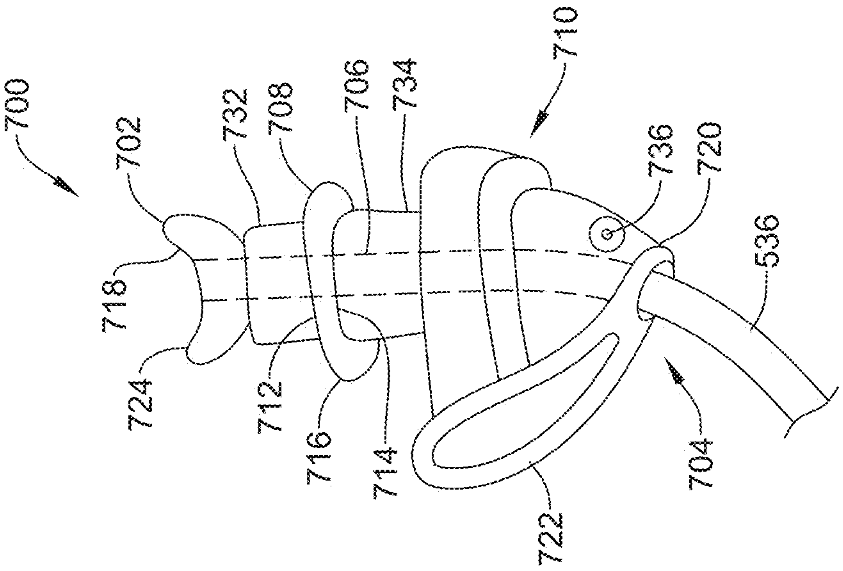
FIG. 7B depicts a perspective view of the illustrative connection system of FIG. 7A in a use configuration.

FIG. 7A depicts a perspective view of another illustrative connection system 700 in an insertion or removal configuration and FIG. 7B depicts a perspective view of the illustrative connection system 700 in a use configuration. The connection system 700 may extend from a first end 702 configured to be inserted into the neck region 508 of the first container 504 to a second end 704 configured to remain outside of the first container 504. For clarity, the first container 504 is not illustrated in FIGS. 7A and 7B. A lumen 706 may extend from the first end 702 to the second end 704 of the connection system 700. The connection system 700 may include a sealing member 708 and a compression member 710. The compression member 710 may be actuatable to move the sealing member 708 between an insertion or removal configuration (FIG. 7A) and a radially expanded use configuration (FIG. 7B).

The scaling member 708 may have a generally tubular body 716 extending from a first end 712 to a second end 714. The sealing member 708 may be formed from a deformable or elastomeric material, such as, but not limited to, silicone, rubbers, thermoplastic elastomers, or other material that allows the sealing member 708 to temporarily deform. The sealing member 708 may be disposed over a portion of the compression member 710, as will be described in more detail herein.

The compression member 710 may extend from a first end 718 to a second end 720. The compression member 710 may include an actuatable handle 722 movably coupled to an end member 724 via an actuation member (not explicitly shown). A first collar 732 may be positioned between the end member 724 and the generally tubular body 716 of the sealing member 708. A second collar 734 may be positioned between the generally tubular body 716 of the sealing member 708 and a head portion 726 of the compression member 710. Said differently, the first end 718 of the compression member 710 may be distal to the first end 712 of the tubular body 716 of the sealing member 708 and the second end 720 of the compression member 710 may be proximal to the second end 714 of the tubular body 716 of the sealing member 708. The head portion 726 may include a hinge 736 to allow the handle 722 to rotate or pivot. In some embodiments, the lumen 706 may extend through the actuation member, although this is not required. In some examples, the lumen 706 may have an opening at the head portion 726 of the compression member 710. In other examples, the lumen 706 may have an opening at the actuatable handle 722, as can be seen in FIG. 7B. A first end of the first fluid supply tube 536 may be fluidly coupled to the lumen 706 adjacent to the second end 704 of the connection system 700.

As the actuatable handle 722 is moved between a first or an insertion or removal position or configuration (FIG. 7A) to a second or a use position or configuration (FIG. 7B), the end member 724 may be axially displaced. For example, the actuatable handle 722 may be rotated or pivoted towards the head portion 726 of the compression member 710, as shown at arrow 728, to move the compression member 710 from the insertion or removal configuration to the use configuration. As the actuatable handle 722 is rotated or pivoted, the end member 724 is actually displaced towards the head portion 726, as shown at arrow 730. Axially movement of the end member 724 is translated to the first collar 732. As the first collar 732 is axially displaced, the tubular body 716 of the sealing member 708 may be pinched between the first collar 732 and the second collar 734 causing the tubular body 716 to buckle and radially expand, as shown in FIG. 7B.

In some embodiments, the tubular body 716 of the sealing member 708 may be disposed over the actuation member extending between the handle 722 and the end member 724. The actuation member may also be disposed under the first and second collars 732, 734. In some examples, the sealing member 708 may include a first portion that extends under the first collar 732 and a second portion that extends under the second collar 734 to movably coupled the sealing member 708 to the compression member 710.

To assemble the connection system 700 with the first container 504, the first container 504 may be placed in an upright configuration (e.g., with the second end 514 pointed up) and the cap 510 removed. The first end 702 of the connection system 700 may be inserted into the neck region 508 of the first container 504 with the connection system 700 in the insertion configuration (e.g., with the sealing member 708 in an unexpanded configuration). It is contemplated that the connection system 700 may be advanced within the neck region 508 until a first end 738 of the head portion 726 contacts an opening of the first container 504. The actuatable handle 722 may then be pivoted to radially expand the sealing member 708. As the sealing member 708 radially expands, an outer surface of the sealing member 708 contacts an inner surface of the neck region 508 to form a fluid-tight seal between the sealing member 708 and the first container 504. Further, the sealing member 708 may frictionally engage the inner surface of the neck region 508 to secure the connection system 700 to the first container 504. The first container 504 may then be inverted (e.g., with the second end 514 pointed down) to fluidly couple the lumen 706 of the connection system 700 with the fluid in the first container 504 to allow fluid 506 to flow from the first container 504, through the lumen 706 and into the first fluid supply tube 536.

In some embodiments, the connection system 700 may be provided with an air vent (not explicitly shown), similar in form and function to the air vent 642 described with respect to FIG. 6, that allows air to flow into the first container 504 as fluid is 506 is withdrawn from the first container 504. The air vent may help prevent the first container 504 from collapsing under vacuum and/or prevent a vacuum vapor lock which may prevent or make it more difficult to extract fluid 506 from the first container 504. The air vent may be a passageway extending from the first end 702 to the second end 704 of the connection system 700 to fluidly connect the interior of the first container 504 with atmosphere. A hydrophobic filter may be positioned at an opening of the air vent or within the passageway thereof to prevent fluid 506 from leaking from the first container 504 while allowing air to enter. Alternatively, or additionally, it is contemplated that the air vent may extend through the compression member 710. In some embodiments, in place of or in addition to the air vent, a hole may be punctured into the first end 512 or a sidewall above the water line of the container to allow air to enter the first container 504 as fluid exits. In other examples, the connection system 700 may include a vent tube that extends above the fluid line to the air headspace similar in form and function to the vent tube 840 described with respect to FIG. 8B.

If the first reservoir 502 needs to be replaced, the first reservoir 502 may be positioned upright (e.g., with the second end 514 pointed up) to avoid or limit leakage or spills. The actuatable handle 722 may be pivoted or rotated away from head portion 726 to axially displace the end member 724 in a direction away from the head portion 726. This may allow the tubular body 716 of the sealing member 708 to resume the unbuckled or unexpanded configuration. The connection system 700 may then be removed from the first reservoir 502. The connection system 700 may then be inserted into a different full reservoir in the manner described herein.

Figure 8A:
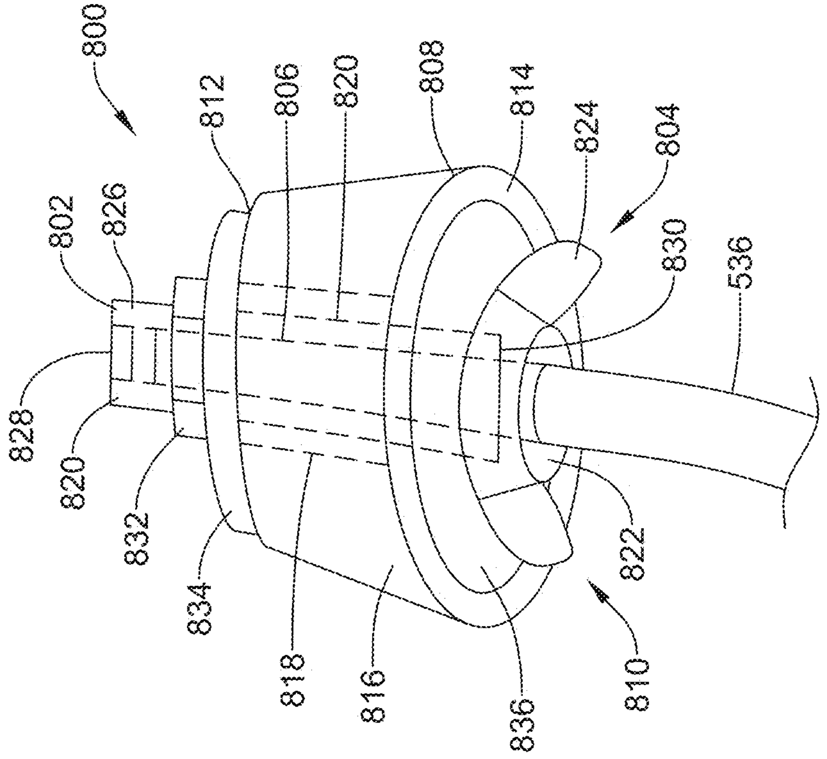
FIG. 8A depicts a perspective view of another illustrative connection system in an insertion or removal configuration.

FIG. 8A depicts a perspective view of another illustrative connection system 800 in an insertion or removal configuration. The connection system 800 may extend from a first end 802 configured to be inserted into the neck region 508 of the first container 504 to a second end 804 configured to remain outside of the first container 504. For clarity, the first container 504 is not illustrated in FIG. 8A. A lumen 806 may extend from the first end 802 to the second end 804 of the connection system 800. The connection system 800 may include a sealing member 808 and a compression member 810. The compression member 810 may be actuatable to move the sealing member 808 between an insertion or removal configuration (FIG. 8A) and a radially expanded use configuration (not explicitly shown).

The sealing member 808 may have a body 816 extending from a first end 812 to a second end 814. The body 816 may take the shape of a truncated cone with the diameter decreasing from the second end 814 to the first end 812. A lumen 818 may extend from the first end 812 to the second end 814 of the sealing member 808. The sealing member 808 may be formed from a deformable or elastomeric material, such as, but not limited to, silicone, rubbers, thermoplastic elastomers, or other material that allows the sealing member 808 to temporarily deform. The sealing member 808 may be disposed over or surround a portion of the compression member 810, as will be described in more detail herein.

The compression member 810 may extend from a first end 820 to a second end 822. The compression member 810 may include an actuatable member 824 movably coupled to a tubular member 826. The tubular member 826 may define the lumen 806 and may extend from a first end 828 positioned distal to the first end 812 of the sealing member 808 through the lumen 818 of the sealing member 808 to a second end 830 coupled to the actuatable member 824. A first end of the first fluid supply tube 536 may be fluidly coupled to the lumen 806 adjacent to the second end 830 of the tubular member 826. In some embodiments, the tubular member 826 may include a plurality of external threads and the actuatable member 824 may be an internally threaded component, such as, but not limited to, a nut, or wing nut. A securing member 832, such as, but not limited to, a nut, may be coupled to the tubular member 826 adjacent the first end 828 thereof. A first retaining member 834, such as, but not limited to an annular washer, may be positioned between the securing member 832 and the first end 812 of the scaling member 808. A second retaining member 836, such as, but not limited to an annular washer, may be positioned between the actuatable member 824 and the second end 814 of the sealing member 808. The first and second retaining members 834, 836 may include a central opening sized to allow the tubular member 826 to pass therethrough while precluding the actuatable member 824 and/or the securing member 832 from passing through the lumen 818 of the sealing member 808. Said differently, the tubular member 826 may pass thorough the lumen 818 of the sealing member with the first end 820 of the compression member 810 distal to the first end 812 of the body 816 of the sealing member 808 and the second end 822 of the compression member 810 proximal to the second end 814 of the body 816 of the sealing member 808.

The actuatable member 824 may be rotatably coupled to the tubular member 826 (e.g., internal threads of the actuatable member 824 may threadably engage the external threads of the tubular member 826). The actuatable member 824 may be rotated in a first direction to move the actuatable member 824 towards or closer to the securing member 832. This movement may exert a biasing force on the sealing member 808 causing the body 816 thereof to compress or buckle and radially expand. The actuatable member 824 may be rotated in a second direction opposite the first direction to move the actuatable member 824 away from or farther from the securing member 832. This movement may allow the body 816 of the sealing member 808 to lengthen and radially contract (or assume its unbiased configuration). In some embodiments, the first rotational direction may be clockwise and the second rotational direction may be counterclockwise. The reverse configuration is also contemplated in which the first rotational direction may be counterclockwise and the second rotational direction may be clockwise. As the actuatable member 824 is rotated, the securing member 832 may prevent the tubular member 826 from rotating which allows the actuatable member 824 to move towards or away from the securing member 832. In some embodiments, the first and second retaining members 834, 836 may spread the compressive force of the actuatable member 824 over a greater surface area of the first and/or second ends 812, 814 of the sealing member 808 to facilitate compression or buckling of the body 816.

To assemble the connection system 800 with the first container 504, the first container 504 may be placed in an upright configuration (e.g., with the second end 514 pointed up) and the cap 510 removed. The first end 802 of the connection system 800 may be inserted into the neck region 508 of the first container 504 with the connection system 800 in the insertion configuration (e.g., with the sealing member 808 in an unexpanded configuration). It is contemplated that the connection system 800 may be advanced within the neck region 508 until a portion of the sealing member 808 frictionally engages an inner surface of the neck region 508. The actuatable member 824 may then be rotated in a first direction to buckle and radially expand the sealing member 808. As the sealing member 808 radially expands, an outer surface of the sealing member 808 contacts an inner surface of the neck region 508 to form a fluid-tight seal between the sealing member 808 and the first container 504. Further, the sealing member 808 may frictionally engage the inner surface of the neck region 508 to secure the connection system 800 to the first container 504. The first container 504 may then be inverted (e.g., with the second end 514 pointed down) to fluidly couple the lumen 806 of the connection system 800 with the fluid in the first container 504 to allow fluid 506 to flow from the first container 504, through the lumen 806 and into the first fluid supply tube 536.

While the sealing member 808 has been described as having a generally truncated conical shape, it is contemplated that other shapes may be used as desired. In some examples, the sealing member 808 may have a cylindrical outer profile that is greater than an inner diameter of the neck region 508 of the container. For example, the scaling member 808 may be a gasket. In such an instance, the compression member 810 may be configured to bias the sealing member 808 against the surface of the opening of the first container 504.

In some embodiments, the connection system 800 may be provided with an air vent (not explicitly shown), similar in form and function to the air vent 642 described with respect to FIG. 6, that allows air to flow into the first container 504 as fluid is 506 is withdrawn from the first container 504. The air vent may help prevent the first container 504 from collapsing under vacuum and/or prevent a vacuum vapor lock which may prevent or make it more difficult to extract fluid 506 from the first container 504. The air vent may be a passageway extending from the first end 802 to the second end 804 of the connection system 800 to fluidly connect the interior of the first container 504 with atmosphere. A hydrophobic filter may be positioned at an opening of the air vent or within the passageway thereof to prevent fluid 506 from leaking from the first container 504 while allowing air to enter. Alternatively, or additionally, it is contemplated that the air vent may extend through the compression member 810. In some embodiments, in place of or in addition to the air vent, a hole may be punctured into the first end 512 or a sidewall above the water line of the container to allow air to enter the first container 504 as fluid exits.

If the first reservoir 502 needs to be replaced, the first reservoir 502 may be positioned upright (e.g., with the second end 514 pointed up) to avoid or limit leakage or spills. The actuatable member 824 may be rotated in a direction opposite the first direction axially displace the actuatable member 824 in a direction away from the securing member 832. This may allow the body 816 of the sealing member 808 to resume the unbuckled or unexpanded configuration. The connection system 800 may then be removed from the first reservoir 502. The connection system 800 may then be inserted into a different full reservoir in the manner described herein.

Figure 8B:
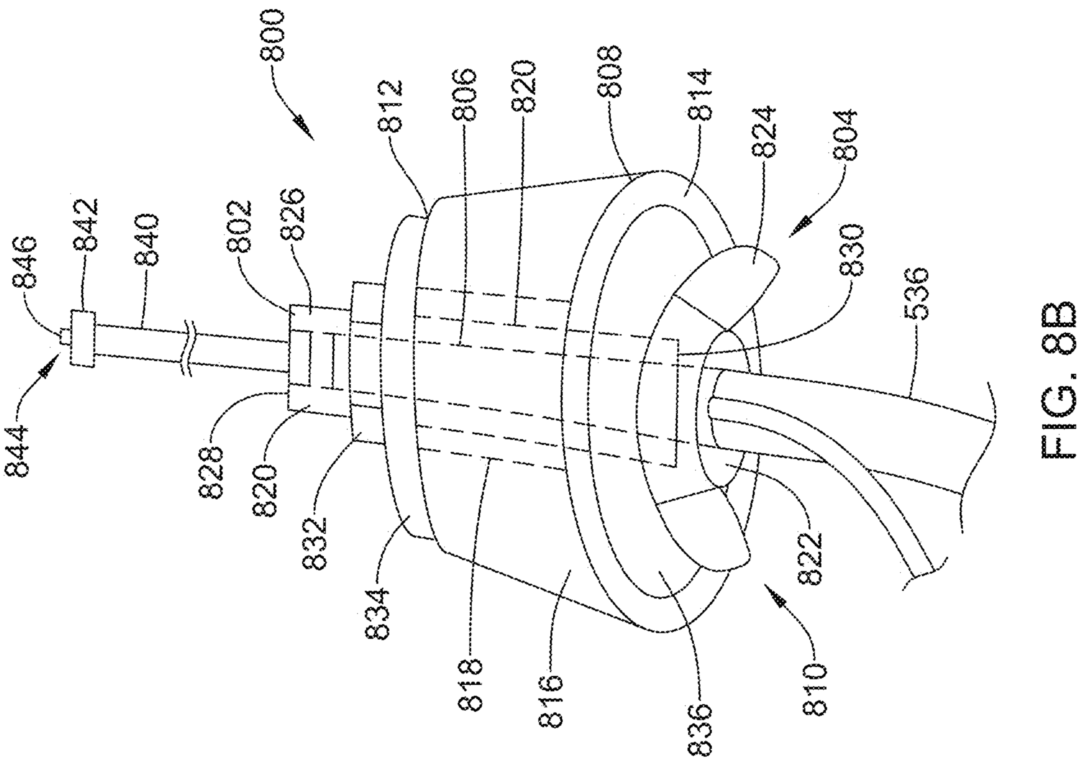
FIG. 8B depicts a perspective view of the illustrative connection system of FIG. 8A including a vent tube.

FIG. 8B depicts a perspective view of the illustrative connection system 800 of FIG. 8A including a vent tube 840. It is contemplated that as fluid 506 exits the first container 504, air may be allowed to enter the first container 504 via the vent tube 840 to prevent the first container 504 from collapsing or creating a water lock (which may prevent the first container 504 from emptying). In some examples, a vent tube 840 may extend through the lumen 806 of the connection system 800 or along an exterior of the tubular member 826. The vent tube 840 may include a floating member 842 positioned at a first end thereof. The floating member 842 may be formed as a single monolithic structure with the vent tube 840 or may be formed as a separate member and subsequently coupled with the vent tube 840. The floating member 842 may have a density less than a density of the fluid 506 in the first container 504 to allow the floating member 842 to float above the fluid line of the fluid 506 in the first container 504. The vent tube 840 and the floating member 842 may have a lumen 844 extending from a first end of the floating member 842 to a second end of the vent tube 840 which is open to atmosphere. Air may enter the vent tube 840 at the second end thereof and exit into the first container 504 via an opening 846 in the vent tube 840 which is positioned above the fluid line and as the opening 846 of the vent tube 840 is positioned above the fluid line in the air headway, fluid is precluded from exiting the first container 504 via the vent tube 840. In some embodiments, the floating member 842 may be omitted. In such an instance, the vent tube 840 may have a length that positions the opening 846 at the first end of the vent tube 840 above the fluid line.

Figure 9:
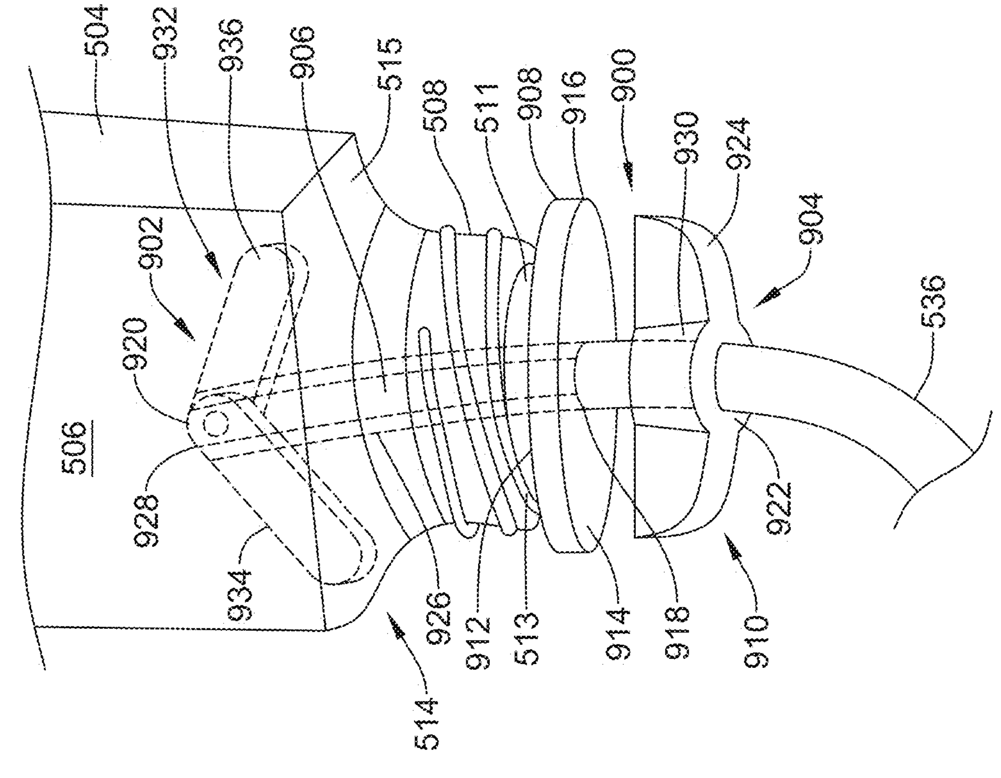
FIG. 9 depicts a perspective view of another illustrative connection system and container with the connection system in a partially deployed configuration.

FIG. 9 depicts a perspective view of another illustrative connection system 900 in a partially deployed configuration. The connection system 900 may extend from a first end 902 configured to be inserted into the neck region 508 of the first container 504 to a second end 904 configured to remain outside of the first container 504. A lumen 906 may extend from the first end 902 to the second end 904 of the connection system 900. The connection system 900 may include a sealing member 908 and a compression member 910. The compression member 910 may be actuatable to move the scaling member 908 against the rim 513 of the first container 504 to fluidly seal the opening 511 of the first container 504.

The sealing member 908 may have a body 916 extending from a first end 912 to a second end 914. The body 916 may be generally annular with an outer diameter that is greater than an outer diameter of the opening 511 of the first container 504. An aperture 918 may extend from the first end 912 to the second end 914 of the sealing member 908. The scaling member 908 may be formed from a deformable or elastomeric material, such as, but not limited to, silicone, rubbers, thermoplastic elastomers, or other material that allows the sealing member 908 to temporarily deform. The sealing member 908 may be disposed over or surround a portion of the compression member 910, as will be described in more detail herein.

The compression member 910 may extend from a first end 920 to a second end 922. The compression member 910 may include an actuatable member 924 movably coupled to a tubular member 926. The tubular member 926 may define the lumen 906 and may extend from a first end 928 positioned distal to the first end 912 of the sealing member 908 through the aperture 918 of the sealing member 908 to a second end 930 coupled to the actuatable member 924. A first end of the first fluid supply tube 536 may be fluidly coupled to the lumen 906 adjacent to the second end 930 of the tubular member 926. In some embodiments, the tubular member 926 may include a plurality of external threads and the actuatable member 924 may be an internally threaded component, such as, but not limited to, a nut, a wing nut, or other rotatable member. A securing member 932, such as, but not limited to, an expanding truss, may be coupled to the tubular member 926 adjacent the first end 928 thereof. The securing member 932 may include a first arm 934 and a second arm 936. The first and second arms 934, 936 may be movable between a first insertion or removal configuration in which the first and second arms 934, 936 are folded down against an outer surface of the tubular member 926 and a use configuration in which the first and second arms 934, 936 extend radially outward from the tubular member 926. As will be described in more detail herein, in the use configuration the first and second arms 934, 936 may have an outermost radial dimension that is greater than an inner diameter of the neck region 508 such that the first and second arms 934, 936 contact an internal surface of a wider region of the interior of the first container 504.

While not explicitly shown, in some embodiments, a retaining member, such as, but not limited to, an annular washer, may be positioned between the actuatable member 924 and the second end 914 of the sealing member 908. If so provided, the retaining member may include a central opening sized to allow the tubular member 926 to pass therethrough while precluding the actuatable member 924 and/or the securing member 932 from passing through the aperture 918 of the sealing member 908.

The actuatable member 924 may be rotatably coupled to the tubular member 926 (e.g., internal threads of the actuatable member 924 may threadably engage the external threads of the tubular member 926). The actuatable member 924 may be rotated in a first direction to move the actuatable member 924 towards or closer to the securing member 932. Rotation of the actuatable member 924 in the first direction may also move the first and second arms 934, 936 into the radially extended configuration. As the first and second arms 934, 936 radially extend and the actuatable member 924 is moved towards the securing member, the sealing member 908 may be brought towards and into contact with the rim 513 of the first container 504. Rotation of the actuatable member 924 may be continued until the sealing member 908 compresses against the rim 513 to form a fluid-tight seal therewith. The actuatable member 924 may be rotated in a second direction opposite the first direction to move the actuatable member 924 away from or farther from the securing member 932 and to move the first and second arms 934, 936 towards the tubular member 926. This movement may allow the sealing member 908 to move away from the rim 513 of the first container 504 and/or the connection system 900 to be removed from the first container 504. In some embodiments, the first rotational direction may be clockwise and the second rotational direction may be counterclockwise. The reverse configuration is also contemplated in which the first rotational direction may be counterclockwise and the second rotational direction may be clockwise. In some embodiments, if so provided, the retaining member may spread the compressive force of the actuatable member 924 over a greater surface area of the scaling member 908 to facilitate compression of the sealing member 908 against the rim 513.

To assemble the connection system 900 with the first container 504, the first container 504 may be placed in an upright configuration (e.g., with the second end 514 pointed up) and the cap 510 removed. The first end 902 of the connection system 900 may be inserted into the neck region 508 of the first container 504 with the connection system 900 in the insertion configuration (e.g., with the first and second arms 934, 936 extending generally parallel to and along an outer surface of the tubular member 926). It is contemplated that the connection system 900 may be advanced within the neck region 508 until the first and second arms 934, 936 are beyond the neck region 508. The actuatable member 924 may then be rotated in a first direction to extend the first and second arms 934, 936 and the compress the sealing member 908 against the rim 513. As the sealing member 908 compresses against the rim 513, a fluid-tight seal is formed between the sealing member 908 and the first container 504.

The first container 504 may then be inverted (e.g., with the second end 514 pointed down) to fluidly couple the lumen 906 of the connection system 900 with the fluid in the first container 504 to allow fluid 506 to flow from the first container 504, through the lumen 906 and into the first fluid supply tube 536.

In some embodiments, the connection system 900 may be provided with an air vent (not explicitly shown), similar in form and function to the air vent 642 described with respect to FIG. 6, that allows air to flow into the first container 504 as fluid is 506 is withdrawn from the first container 504. The air vent may help prevent the first container 504 from collapsing under vacuum and/or prevent a vacuum vapor lock which may prevent or make it more difficult to extract fluid 506 from the first container 504. The air vent may be a passageway extending from the first end 902 to the second end 904 of the connection system 900 to fluidly connect the interior of the first container 504 with atmosphere. A hydrophobic filter may be positioned at an opening of the air vent or within the passageway thereof to prevent fluid 506 from leaking from the first container 504 while allowing air to enter. Alternatively, or additionally, it is contemplated that the air vent may extend through the compression member 910. In some embodiments, in place of or in addition to the air vent, a hole may be punctured into the first end 512 or a sidewall above the water line of the container to allow air to enter the first container 504 as fluid exits. In other examples, the connection system 900 may include a vent tube that extends above the fluid line to the air headspace similar in form and function to the vent tube 840 described with respect to FIG. 8B.

If the first reservoir 502 needs to be replaced, the first reservoir 502 may be positioned upright (e.g., with the second end 514 pointed up) to avoid or limit leakage or spills. The actuatable member 924 may be rotated in a direction opposite the first direction axially displace the actuatable member 924 in a direction away from the securing member 932 and to radially collapse the first and second arms 934, 936 towards the tubular member 926. This may allow the connection system 900 to be removed from the first reservoir 502. The connection system 900 may then be inserted into a different full reservoir in the manner described herein.

Figure 10:
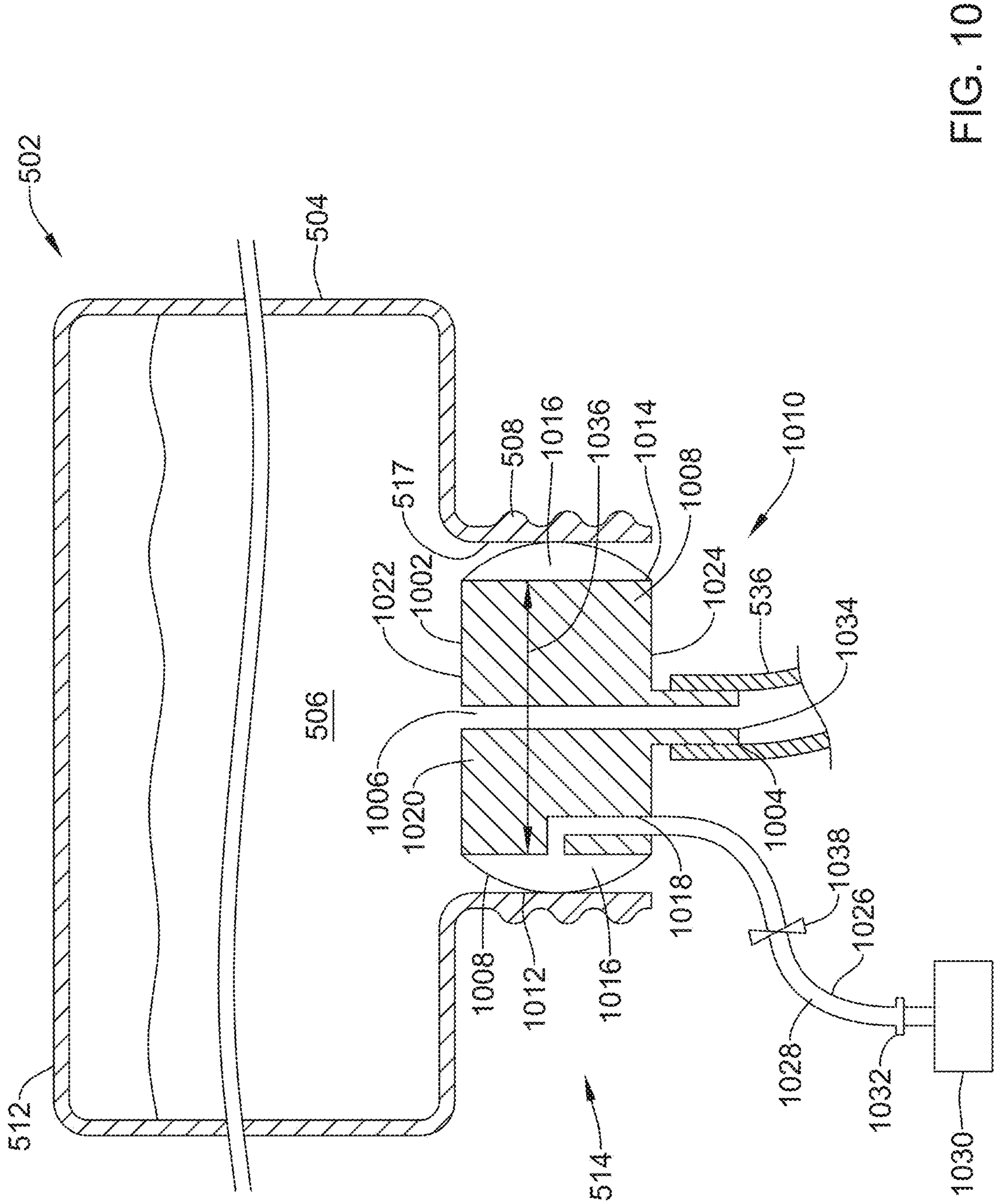
FIG. 10 depicts a schematic cross-sectional view of another illustrative connection system a container with the connection system in a deployed configuration.

FIG. 10 depicts a schematic cross-sectional view of another illustrative connection system 1000 in a deployed configuration. The connection system 1000 may extend from a first end 1002 configured to be inserted into the neck region 508 of the first container 504 to a second end 1004 configured to remain outside of the first container 504. A lumen 1006 may extend from the first end 1002 to the second end 1004 of the connection system 1000. The connection system 1000 may include a sealing member 1008 and a plug 1010. The sealing member 1008 may be expandable to move the sealing member 1008 against the inner surface 517 of neck region 508 of the first container 504 to fluidly seal connection system 1000 and the first container 504.

The sealing member 1008 may include an expandable balloon 1012 coupled or bonded to an outer surface 1014 of the plug 1010. The expandable balloon 1012 may define a cavity 1016 configured to receive an inflation fluid. The inflation fluid may be air, saline, or other suitable fluid. When the inflation fluid is received within the cavity 1016 of the expandable balloon 1012, the expandable balloon 1012 may expand or inflate, as shown in FIG. 10. When inflation fluid is removed from the cavity 1016 thereof, the expandable balloon 1012 deflates or collapses. The expandable balloon 1012 may be formed from compliant or semi-compliant materials, such as, but not limited to latex, thermoplastic elastomers, polyethylene terephthalate (PET), nylons, polyurethanes, silicone, polyether block amides (such as, but not limited to, PEBAX®), higher durometer polyurethanes, etc. The expandable balloon 1012 may extend about an entirety of the circumference of the plug 1010 to form a seal around an entire perimeter of the neck region 508. The expandable balloon 1012 may extend along an entirety of a length of the plug 1010 or less than an entirety of the length, as desired.

An inflation lumen 1018 may extend through a body 1020 of the plug 1010. For example, the inflation lumen 1018 may extend from a second end 1024 of plug 1010 towards a first end 1022 of the plug 1010. Prior to reaching the first end 1022 of the plug 1010, the inflation lumen 1018 may bend or be angled towards the lateral outer surface 1014 of the plug 1010. While the inflation lumen 1018 is illustrated as including a generally 90° bend, the bend may be less than 90° or greater than 90°, as desired. The inflation lumen 1018 may be coupled to an inflation tube 1026. The inflation tube 1026 may define a lumen 1028 having a first end in fluid communication with the inflation lumen 1018 interior of the expandable balloon 1012 and a second end 1032 in fluid communication with an inflation source 1030. The second end 1032 may include an inflation port with a standard luer lock features such that it would be compatible with the luer features universally used on medical syringes, although this is not required. The inflation source 1030 may be a syringe, a ball bladder, or other fluid source. A valve, stopcock, or other flow control mechanism 1038 may be positioned in-line with the inflation tube 1026. The flow control mechanism 1038 may be actuatable between an open configuration in which fluid may flow through the lumen of the inflation tube 1026 to enter or exit an interior 1016 of the expandable balloon 1012 and a closed configuration in which fluid is prevented from flowing through the lumen of the inflation tube 1026 to enter or exit an interior of the expandable balloon 1012.

The body 1020 of the plug 1010 may extend from a first end 1022 to a second end 1024. The plug 1010 may be formed from a flexible or rigid material, as desired, such as, but not limited to, silicone, rubber, thermoplastic elastomers, polycarbonate, acrylonitrile butadiene styrene (ABS), or other suitable materials. In some examples, an outer diameter 1036 of the plug 1010 may taper or decrease along at least a portion of the length thereof. In some examples, the outer diameter 1036 may decrease from a location adjacent to the second end 1024 of the body 1020 to the first end 1022. It is contemplated that the tapered outer diameter 1036 may facilitate assembly of the plug 1010 with the first container 504. Further, the tapered outer diameter 1036 may allow the plug 1010 to interface with containers 504 having different internal neck diameters. An outer diameter 1036 of the plug 1010 adjacent to the first end 1022 thereof may be less than an inner diameter of the neck region 508 of the first container 504 to allow the first end 1022 of the plug 1010 to be inserted into the neck region 508 with little or no resistance while the outer diameter 1036 of the plug 1010 adjacent to the second end 1024 may be greater than an inner diameter of the neck region 508 to limit advancement of the plug 1010 into the first container 504 and/or to facilitate the formation of a fluid-tight seal with the first container 504, although this is not required. However, in other embodiments the outer diameter 1036 of the plug 1010 may be approximately constant from a location adjacent to the second end 1024 to the first end 1022.

The second end 1024 of the body 1020 may include a port 1034 extending therefrom. The port 1034 may be configured to be fluidly coupled with a first end of the first fluid supply tube 536. In some examples, the port 1034 may be a hose barb including a plurality of raised ribs configured to be disposed within a lumen of the first fluid supply tube 536 and engage an inner surface thereof. In other examples, the port 1034 may be disposed over an outer surface of the first fluid supply tube 536. The port 1034 may have an outer diameter that is sized to couple with the first fluid supply tube 536. In some examples, the outer diameter of the port 1034 may be less than an outer diameter of the body 1020 of the plug 1010. However, this is not required. The lumen 1006 may extend from the first end 1022 of the body 1020 to the port 1034 to fluidly couple an interior of the first container 504 with the first fluid supply tube 536.

To assemble the connection system 1000 with the first container 504, the first container 504 may be placed in an upright configuration (e.g., with the second end 514 pointed up) and the cap 510 removed. The first end 1002 of the connection system 1000 may be inserted into the neck region 508 of the first container 504 with the expandable balloon 1012 in a deflated or unexpanded configuration. It is contemplated that the connection system 1000 may be advanced within the neck region 508 until the expandable balloon 1012 is within the neck region 508. An inflation fluid may then be passed from the inflation source 1030 through the inflation tube 1026, with the valve 1038 in the open configuration, and into the cavity 1016 of the expandable balloon 1012 to radially expand the expandable balloon 1012. In the expanded configuration the outer surface of the expandable balloon 1012 may contact and form a fluid-tight seal with the inner surface 517 of the neck region 508 of the first container 504. Once the expandable balloon 1012 is expanded, the valve 1038 may be closed to maintain fluid within the cavity 1016 of the expandable balloon 1012 such that the expandable balloon 1012 remains in the expanded configuration. The first container 504 may then be inverted (e.g., with the second end 514 pointed down) to fluidly couple the lumen 1006 of the connection system 1000 with the fluid in the first container 504 to allow fluid 506 to flow from the first container 504, through the lumen 1006 and into the first fluid supply tube 536.

In some embodiments, the connection system 1000 may be provided with an air vent (not explicitly shown), similar in form and function to the air vent 642 described with respect to FIG. 6, that allows air to flow into the first container 504 as fluid is 506 is withdrawn from the first container 504. The air vent may help prevent the first container 504 from collapsing under vacuum and/or prevent a vacuum vapor lock which may prevent or make it more difficult to extract fluid 506 from the first container 504. The air vent may be a passageway extending from the first end 1002 to the second end 1004 of the connection system 1000, such as through the plug 1010, to fluidly connect the interior of the first container 504 with atmosphere. A hydrophobic filter may be positioned at an opening of the air vent or within the passageway thereof to prevent fluid 506 from leaking from the first container 504 while allowing air to enter. In some embodiments, in place of or in addition to the air vent, a hole may be punctured into the first end 512 or a sidewall above the water line of the container to allow air to enter the first container 504 as fluid exits. In other examples, the connection system 1000 may include a vent tube that extends above the fluid line to the air headspace similar in form and function to the vent tube 840 described with respect to FIG. 8B.

If the first reservoir 502 needs to be replaced, the first reservoir 502 may be positioned upright (e.g., with the second end 514 pointed up) to avoid or limit leakage or spills. The valve 1038 may be moved to the open configuration to allow pressure or fluid to dissipate from or exit the cavity 1016 of the expandable balloon 1012 to radially collapse the expandable balloon 1012. This may allow the connection system 1000 to be removed from the first reservoir 502. The connection system 1000 may then be inserted into a different full reservoir in the manner described herein.

Figure 11:
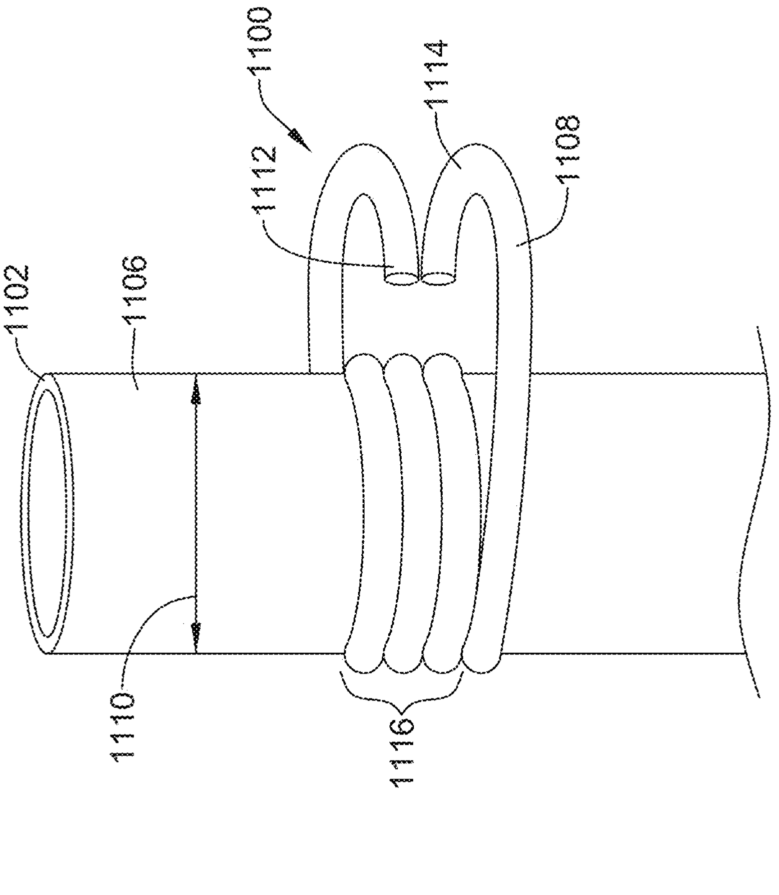
FIG. 11 depicts a perspective view of another illustrative connection system.

FIG. 11 depicts a perspective view of another illustrative connection system 1100. For clarity, the first container 504 is not illustrated in FIG. 11. The connection system 1100 may extend from a first end 1102 configured to be inserted into the neck region 508 of the first container 504 to a second end (not explicitly shown) configured to remain outside of the first container 504. A lumen 1104 may extend from the first end 1102 to the second end of the connection system 1100. The connection system 1100 may include an elongate tubular member 1106 and a compression member 1108. The elongate tubular member 1106 may be temporarily compressed to move the elongate tubular member 1106 into the neck region 508 and then allowed to expand against the inner surface 517 of neck region 508 of the first container 504 to fluidly seal connection system 1100 and the first container 504.

The elongate tubular member 1106 may be formed from an elastomeric or compressible material that allows the elongate tubular member 1106 to be squeezed or compressed to reduce an outer diameter thereof while returning to an unbiased or uncompressed configuration in the absence of the squeezing force. The elongate tubular member 1106 may have an outer diameter 1110 in the unbiased or uncompressed configuration that is greater than an inner diameter of the neck region 508 of the first container 504 so that when the elongate tubular member 1106 is positioned within the neck region 508, the outer surface of the elongate tubular member 1106 pushes against the inner surface 517 of the neck region 508 to form a fluid tight seal therewith. In some examples, in the unbiased or uncompressed configuration, the outer diameter 1110 of the elongate tubular member 1106 may taper or reduce from the first end 1102 of the connection system 1100 to the second end thereof. However, this is not required. In some examples, the elongate tubular member 1106 may be formed as a single monolithic structure with the first fluid supply tube 536. In other examples, the elongate tubular member 1106 may be formed as a separate element from the first fluid supply tube 536 and may be fixedly or removably coupled or attached to the first fluid supply tube 536.

The compression member 1108 may include an actuatable clamp including a first gripping member 1112, a second gripping member 1114, and a plurality of helically wound coils 1116 disposed between the first gripping member 1112 and the second gripping member 1114. The plurality of helically wound coils 1116 may extend or wind about an outer surface of the elongate tubular member 1106 adjacent to the first end of the connection system 1100. While the compression member 1108 is illustrated as including approximately three helically wound coils 1116, the compression member 1108 may include fewer than three or more than three helically wound coils 1116, as desired. The compression member 1108 may be configured such that squeezing the first gripping member 1112 and the second gripping member 1114 towards one another causes the inner diameter of the plurality of helically wound coils 1116 to compress or reduce and exert a squeezing or compressing force on the elongate tubular member 1106 to reduce an outer diameter thereof. In some cases, the first gripping member 1112 and the second gripping member 1114 may be moved away from one another to reduce the inner diameter of the plurality of helically wound coils 1116. It is further contemplated that the first gripping member 1112 and/or the second gripping member 1114 may be angled or configured to extend away from the first end 1102 of the connection system 1100 to allow a portion of the compression member 1108 to be disposed within the neck region 508 of the first container 504 while maintaining access to the first gripping member 1112 and the second gripping member 1114.

To assemble the connection system 1100 with the first container 504, the first container 504 may be placed in an upright configuration (e.g., with the second end 514 pointed up) and the cap 510 removed. The first gripping member 1112 and the second gripping member 1114 may be actuated to compress the elongate tubular member 1106 and temporarily reduce the outer diameter 1110 of the elongate tubular member 1106. The compression member 1108 may be positioned close enough to the first end 1102 of the connection system 1100 to compress the first end 1102 of the connection system 1100. With the elongate tubular member 1106 in the compressed configurations, the first end 1102 of the connection system 1100 may then be inserted into the neck region 508 of the first container 504. The biasing force on the compression member 1108 may then be released allowing the elongate tubular member 1106 to return to an uncompressed outer diameter. In the unbiased configuration, the outer surface of the elongate tubular member 1106 may contact and form a fluid-tight seal with the inner surface 517 of the neck region 508 of the first container 504. Once the elongate tubular member 1106 returns to its original configuration, the first container 504 may then be inverted (e.g., with the second end 514 pointed down) to fluidly couple the lumen 1104 of the connection system 1100 with the fluid in the first container 504 to allow fluid 506 to flow from the first container 504, through the lumen 1104 and into the first fluid supply tube 536.

In some embodiments, the connection system 1100 may be provided with an air vent (not explicitly shown), similar in form and function to the air vent 642 described with respect to FIG. 6, that allows air to flow into the first container 504 as fluid is 506 is withdrawn from the first container 504. The air vent may help prevent the first container 504 from collapsing under vacuum and/or prevent a vacuum vapor lock which may prevent or make it more difficult to extract fluid 506 from the first container 504. The air vent may be a passageway extending from the first end 1102 to the second end of the connection system 1100 to fluidly connect the interior of the first container 504 with atmosphere. A hydrophobic filter may be positioned at an opening of the air vent or within the passageway thereof to prevent fluid 506 from leaking from the first container 504 while allowing air to enter. In some embodiments, in place of or in addition to the air vent, a hole may be punctured into the first end 512 or a sidewall above the water line of the container to allow air to enter the first container 504 as fluid exits. In other examples, the connection system 1100 may include a vent tube that extends above the fluid line to the air headspace similar in form and function to the vent tube 840 described with respect to FIG. 8B.

If the first reservoir 502 needs to be replaced, the first reservoir 502 may be positioned upright (e.g., with the second end 514 pointed up) to avoid or limit leakage or spills. The compression member 1108 may be squeezed or biased to reduce the diameter of the elongate tubular member 1106. This may allow the connection system 1100 to be removed from the first reservoir 502. The connection system 1100 may then be inserted into a different full reservoir in the manner described herein.

As will be appreciated, the lengths of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of 9.7 mm. The lens wash supply tubing may have an inner diameter of approximately 5 mm and an outer diameter of 8 mm. The gas supply tubing may have an inner diameter of approximately 2 mm and an outer diameter of 3.5 mm. The alternative gas supply tubing may have an inner diameter of approximately 5 mm and an outer diameter of 8 mm.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed is:

1. A container and tube set arranged and configured to couple to an endoscope for use in an endoscopic procedure, the container and tube set comprising:

a first container including a neck defining an opening and a body portion, the first container configured to contain a fluid;

a sealing member including a first end, a second end, and a first lumen extending therethrough, the sealing member configured to be disposed adjacent to the opening of the neck of the first container;

a compression member including a first end, a second end, and a second lumen extending therethrough, the compression member configured to selectively expand the sealing member;

a first fluid supply tube including a first end, a second end, and a third lumen extending therethrough, wherein the third lumen is in fluid communication with the first container, the first end is coupled to the second end of the compression member, and the second end of the first water supply tube is positioned external to the first container;

a branched connector positioned in line with the first fluid supply tube, the branched connector including a first fluid inlet, a first fluid outlet, and a second fluid outlet, a portion of the third lumen of the first fluid supply tube extending between the first fluid inlet and the first fluid outlet;

a second container configured to contain a fluid, the second container having a second fluid inlet in selective fluid communication with the third lumen of the first fluid supply tube;

a second fluid supply tube including a first end, a second end, and a fourth lumen extending therethrough, wherein the fourth lumen is in selective fluid communication with a bottom portion of the second container and the second end of the second water supply tube is positioned external to the second container; and a first gas supply tube including a first end, a second end, and a fifth lumen extending therethrough, wherein the fifth lumen is in operative fluid communication with the second container and the second end of the first gas supply tube is positioned external to the second container.

2. The container and tube set of claim 1, further comprising:

a third fluid supply tube including a first end, a second end, and a sixth lumen extending therethrough, wherein the sixth lumen is in selective fluid communication with the first container, wherein the sixth lumen of the third fluid supply tube in fluid communication with the second outlet.

3. The container and tube set of claim 1, wherein the sealing member comprises an elastomeric material.

4. The container and tube set of claim 1, wherein the sealing member is disposed within the opening of the neck of the first container.

5. The container and tube set of claim 1, wherein the sealing member is positioned against the opening of the neck of the first container.

6. The container and tube set of claim 1, wherein the compression member is disposed within the first lumen of the sealing member.

7. The container and tube set of claim 6, wherein the compression member comprises a rigid material.

8. The container and tube set of claim 6, wherein the compression member has an outer diameter that is greater than an inner diameter of the first lumen of the sealing member along at least a portion of a length of the compression member.

9. The container and tube set of claim 1, wherein the first end of the compression member is positioned distal to the first end of the sealing member and the second end of the compression member is positioned proximal to the second end of the sealing member.

10. The container and tube set of claim 9, wherein the compression member comprises an actuatable member adjacent to the second end thereof.

11. The container and tube set of claim 10, wherein actuation of the actuatable member from a first position to a second position is configured to compress and radially expand the sealing member.

12. The container and tube set of claim 10, wherein the actuatable member is rotated.

13. The container and tube set of claim 10, wherein the actuatable member is pivoted.

14. The container and tube set of claim 1, further comprising a vent tube including a first end, a second end, and a fifth lumen, the vent tube extending through the third lumen of the first fluid supply tube.

15. The container and tube set of claim 14, wherein the first end of the vent tube is configured to extend above a fluid line of the first container.

16. A container and tube set arranged and configured to couple to an endoscope for use in an endoscopic procedure, the container and tube set comprising:

a first container including a neck defining an opening and a body portion, the first container configured to contain a fluid;

an elastomeric sealing member including a first end having a first outer diameter, a second end having a second outer diameter less than the first outer diameter, and a first lumen extending therethrough and having an inner diameter that tapers from the second end to the first end, the elastomeric sealing member configured to be disposed within the opening of the neck of the first container;

a rigid compression member including a first end, a second end, and a second lumen extending therethrough, the rigid compression member disposed within the first lumen of the elastomeric sealing member;

a first fluid supply tube including a first end, a second end, and a third lumen extending therethrough, wherein the third lumen is in fluid communication with the first container, the first end is coupled to the second end of the rigid compression member, and the second end of the first fluid supply tube is positioned external to the first container;

a branched connector positioned in line with the first fluid supply tube between the first and second ends thereof, the branched connector including a first fluid inlet, a first fluid outlet, and a second fluid outlet, a portion of the third lumen of the first fluid supply tube extending between the first fluid inlet and the first fluid outlet;

a second container configured to contain a fluid, the second container having a second fluid inlet in selective fluid communication with the second fluid outlet of the branched connector;

a second fluid supply tube including a first end, a second end, and a fourth lumen extending therethrough, wherein the fourth lumen is in selective fluid communication with a bottom portion of the second container and the second end of the second fluid supply tube is positioned external to the second container; and a first gas supply tube including a first end, a second end, and a fifth lumen extending therethrough, wherein the fifth lumen is in operative fluid communication with the second container and the second end of the first gas supply tube is positioned external to the second container.

17. The container and tube set of claim 16, wherein an outer surface of the rigid compression member is configured to threadably engage the first lumen of the elastomeric sealing member.

18. The container and tube set of claim 16, wherein a third outer diameter of the rigid compression member is greater than the inner diameter of the first lumen of the elastomeric sealing member along at least a portion of a length of the rigid compression member.

19. The container and tube set of claim 16, further comprising a vent hole extending from the first end to the second end of the elastomeric sealing member and a hydrophobic filter disposed within the vent hole.

20. A container and tube set arranged and configured to couple to an endoscope for use in an endoscopic procedure, the container and tube set comprising:

a first container including a neck defining an opening and a body portion, the first container configured to contain a fluid;

an elastomeric sealing member including a first end, a second end, and a first lumen extending therethrough, the elastomeric sealing member configured to be disposed adjacent to the opening of the neck of the first container;

a rigid compression member including a first end, a second end, and a second lumen extending therethrough, the rigid compression member disposed within the first lumen of the elastomeric sealing member, the first end of the rigid compression member positioned distal to the first end of the elastomeric sealing member and the second end of the rigid compression member positioned proximal to the second end of the elastomeric sealing member;

an actuatable member coupled to the rigid compression member, wherein actuation of the actuatable member from a first position to a second position is configured to compress and radially expand the elastomeric sealing member and actuation of the actuatable member from the second position to the first position is configured to release and radially contract the elastomeric sealing member;

a first fluid supply tube including a first end, a second end, and a third lumen extending therethrough, wherein the third lumen is in fluid communication with the first container, the first end is coupled to the second end of the rigid compression member, and the second end of the first fluid supply tube is positioned external to the first container;

a branched connector positioned in line with the first fluid supply tube between the first and second ends thereof, the branched connector including a first fluid inlet, a first fluid outlet, and a second fluid outlet, a portion of the third lumen of the first fluid supply tube extending between the first fluid inlet and the first fluid outlet;

a second container configured to contain a fluid, the second container having a second fluid inlet in selective fluid communication with the second fluid outlet of the branched connector;

a second fluid supply tube including a first end, a second end, and a fourth lumen extending therethrough, wherein the fourth lumen is in selective fluid communication with a bottom portion of the second container and the second end of the second fluid supply tube is positioned external to the second container; and a first gas supply tube including a first end, a second end, and a fifth lumen extending therethrough, wherein the fifth lumen is in operative fluid communication with the second container and the second end of the first gas supply tube is positioned external to the second container.

* * * * *